United States Patent
Baxter et al.

(10) Patent No.: US 7,358,376 B2
(45) Date of Patent: Apr. 15, 2008

(54) SUBSTITUTED THIOPHENE COMPOUNDS

(75) Inventors: Andrew Baxter, Wymeswold (GB); Stephen Brough, Selston (GB); Alan Faull, Macclesfield (GB); Craig Johnstone, Macclesfield (GB); Thomas McInally, Leics (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/868,884

(22) PCT Filed: Feb. 7, 2001

(86) PCT No.: PCT/SE01/00248

§ 371 (c)(1),
(2), (4) Date: Feb. 5, 2002

(87) PCT Pub. No.: WO01/58890

PCT Pub. Date: Aug. 16, 2001

(65) Prior Publication Data
US 2002/0107252 A1  Aug. 8, 2002

(30) Foreign Application Priority Data
Feb. 12, 2000 (GB) ................................ 0003154.2

(51) Int. Cl.
*A61K 31/381* (2006.01)
*C07D 333/20* (2006.01)

(52) U.S. Cl. ................ 549/69; 514/445; 514/447; 549/63

(58) Field of Classification Search ............ 514/231.5, 514/235.5, 235.8, 236.5, 252.13, 254.01, 514/256, 340–343, 252.01, 252.05, 255.05, 514/370, 377, 397, 398, 426, 422, 447, 471, 514/254, 445; 544/132, 133, 137, 141, 146, 544/366, 367, 372, 238, 405, 403; 546/208, 546/209; 549/59, 60, 64, 65, 68, 69, 63; 548/190, 233, 326
See application file for complete search history.

(56) References Cited

U.S. PATENT DOCUMENTS

| 5,258,357 | A | * | 11/1993 | Muenster et al. ............ 504/193 |
| 5,571,810 | A | * | 11/1996 | Matsuo et al. ............ 514/231.5 |
| 5,679,670 | A | * | 10/1997 | Dean et al. ............... 514/211.1 |
| 7,098,240 | B2 | * | 8/2006 | Griffiths et al. ............. 514/447 |
| 7,125,896 | B2 | * | 10/2006 | Faull et al. .................. 514/336 |
| 2004/0024047 | A1 | * | 2/2004 | Callahan et al. ............ 514/438 |
| 2004/0192943 | A1 | * | 9/2004 | Wan et al. ..................... 549/63 |
| 2004/0242573 | A1 | * | 12/2004 | Faull et al. ............... 514/227.5 |
| 2006/0111431 | A1 | * | 5/2006 | Morley et al. ............... 514/447 |

FOREIGN PATENT DOCUMENTS

| EP | 0 202 538 | | 11/1986 |
| EP | 0 853 083 | A1 | 7/1998 |
| EP | 0 908 456 | A1 | 4/1999 |
| GB | 1 468 012 | | 3/1977 |
| WO | 98/02430 | | 1/1998 |
| WO | WO 98/54116 | | 12/1998 |
| WO | WO 99/46244 | | 9/1999 |
| WO | 02/30353 | A2 * | 10/2000 |
| WO | WO 00/71532 | | 11/2000 |
| WO | WO 01/98290 | | 12/2001 |

OTHER PUBLICATIONS

Du, X. et. al., "Aryl ureas represent a new class of anti-trypanosomal agents." Chemistry & Biology, 2000, vol. 7, No. 9, pp. 733-742.*
Berkow, R. et. al., The Merck Manual, 16th Edition, © 1992, Merck Research Laboratories, Rahway, NJ, pp. 1488 and 2664.*
Zayed, et al. "Studies on 5-aminopyrazole derivatives. Synthesis of some new fused pyrazole derivatives", Monatsh. Chem. 115(4) pp. 431-436 (1984).
Zayed, Ezzat Mohammed, et al., Monatsh Chem. (1984), 115 (4), pp. 431-436, (STN International, File CAPLUS, CAPLUS Accession No. 1984: 454985, Document No. 101: 54985).
Zayed, Ezzat Mohammed, et al., "Studies on 5-aminopyrazole Derivatives. Synthesis of Some New Fused Pyrazole Derivatives," Monatsh Chem. (1984), 115 (4), pp. 431-436.
U.S. Appl. No. 10/484,569, filed Jan. 22, 2004, Faull et al.
U.S. Appl. No. 10/484,645, filed Jan. 22, 2004, Griffiths et al.

* cited by examiner

*Primary Examiner*—James O. Wilson
*Assistant Examiner*—Tamthom N Truong
(74) *Attorney, Agent, or Firm*—Fish & Richardson P.C.

(57) ABSTRACT

The invention relates to heteroaromatic carboxamides of formula (I),

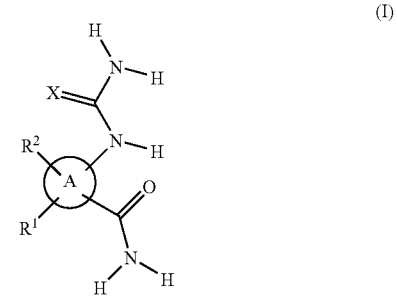

wherein A, $R^1$, $R^2$ and X are as defined in the specification, processes and intermediates used in their preparation, pharmaceutical compositions containing them and their use in therapy.

17 Claims, No Drawings

SUBSTITUTED THIOPHENE COMPOUNDS

FIELD OF THE INVENTION

The present invention relates to heteroaromatic carboxamide derivatives, processes and intermediates used in their preparation, pharmaceutical compositions containing them and their use in therapy.

BACKGROUND OF THE INVENTION

The NF-κB (nuclear factor κB) family is composed of homo- and heterodimers of the Rel family of transcription factors. A key role of these transcription factors is to induce and coordinate the expression of a broad spectrum of pro-inflammatory genes including cytokines, chemokines, interferons, MHC proteins, growth factors and cell adhesion molecules (for reviews see Verma et. al., Genes Dev. 9:2723-35. 1995; Siebenlist et. al., Ann. Rev. Cell. Biol. 10:405-455, 1994; Bauerle and Henkel, Ann. Rev. Immunol., 12:141-179, 1994; Barnes and Karin, New Engl. J. Med., 336:1066-1071, 1997).

The most commonly found Rel family dimer complex is composed of p50 NFkB and p65 RelA (Baeuerle and Baltimore, Cell 53:211-217, 1988; Baeuerle and Baltimore, Genes Dev. 3:1689-1698, 1989). Under resting conditions NF-κB dimers are retained in the cytoplasm by a member of the IκB family of inhibitory proteins (Beg et. al., Genes Dev., 7:2064-2070, 1993; Gilmore and Morin, Trends Genet. 9:427-433, 1993; Haskil et. al., Cell 65:1281-1289, 1991). However, upon cell activation by a variety of cytokines or other external stimuli, IκB proteins become phosphorylated on two critical serine residues (Traenckner et. al., EMBO J., 14:2876, 1995) and are then targeted for ubiquitination and proteosome-mediated degradation (Chen, Z. J. et. al., Genes and Dev. 9:1586-1597, 1995; Scherer, D. C. et. al., Proc. Natl. Acad. Sci. USA 92:11259-11263, 1996; Alkalay, I. et. al., Proc. Natl. Acad. Sci. USA 92:10599-10603, 1995). The released NF-κB is then able to translocate to the nucleus and activate gene transcription (Beg et. al., Genes Dev., 6:1899-1913, 1992).

A wide range of external stimulii have been shown to be capable of activating NF-κB (Baeuerle, P. A., and Baichwal. V. R., Adv. Immunol., 65:111-136, 1997). Although the majority of NF-κB activators result in IκB phosphorylation, it is clear that multiple pathways lead to this key event. Receptor-mediated NF-κB activation relies upon specific interactions between the receptor and adapter/signalling molecules (for example, TRADD. RIP, TRAF, MyD88) and associated kinases (IRAK, NIK) (Song et. al., Proc. Natl. Acad. Sci. USA 94:9792-9796, 1997; Natoli et. al., JBC 272:26079-26082, 1997). Environmental stresses such as UV light and γ-radiation appear to stimulate NF-κB via alternative, less defined, mechanisms.

Recent publications have partially elucidated the NF-κB activation. This work has identified three key enzymes which regulate specific IκB/NF-κB interactions: NF-κB inducing kinase (NIK) (Boldin et. al., Cell 85:803-815, 1996), IκB kinase-1 (IKK-1) (Didonato et. al., Nature 388: 548, 1997; Regnier at. al., Cell 90:373 1997) and IκB kinase-2 (IKK-2) (Woronicz et. al., Science 278:866. 1997; Zandi et. al., Cell 91:243, 1997).

NIK appears to represent a common mediator of NF-κB signalling cascades triggered by tumour necrosis factor and interleukin-1, and is a potent inducer of IκB phosphorylation. However NIK is unable to phosphorylate IκB directly. IKK-1 and IKK-2 are thought to lie immediately downstream of NIK and are capable of directly phosphorylating all three IκB sub-types. IKK-1 and IKK-2 are 52% identical at the amino acid level but appear to have similar substrate specificities; however, enzyme activities appear to be different: IKK-2 is several-fold more potent than IKK-1. Expression data, coupled with mutagenesis studies, suggest that IKK-1 and IKK-2 are capable of forming homo- and heterodimers through their C-terminal leucine zipper motifs, with the heterodimeric form being preferred (Mercurio et. al., Mol. Cell Biol., 19:1526, 1999; Zandi et. al., Science; 281:1360, 1998; Lee et. al. Proc. Natl. Acad. Sci. USA 95:9319, 1998).

NIK, IKK-1 and IKK-2 are all serine threonine kinases. Recent data has shown that tyrosine kinases also play a role in regulating the activation of NF-κB. A number of groups have shown that TNF-α induced NF-κB activation can be regulated by protein tyrosine phosphatases (PTPs) and tyrosine kinases (Amer et. al., JBC 273:29417-29423, 1998: Hu et. al., JBC 273:33561-33565. 1998: Kaekawa et. al., Biochem. J. 337:179-184, 1999: Singh et. al., JBC 271 31049-31054, 1996). The mechanism of action of these enzymes appears to be in regulating the phosphorylation status of IκB. For example, PTP1B and an unidentified tyrosine kinase appear to directly control the phosphorylation of a lysine residue (K42) on IκB-α, which in turn has a critical influence on the accessibility of the adjacent serine residues as targets for phosphorylation by IKK.

Several groups have shown that IKK-1 and IKK-2 form part of a 'signalosome' structure in association with additional proteins including IKAP (Cohen et. al., Nature 395: 292-296, 1998; Rothwarf et. al., Nature 395:297-300, 1998), MEKK-1, putative MAP kinase phosphatase (Lee et. al., Proc. Natl. Acad. Sci. USA 95:9319-9324, 1998), as well as NIK and IκB. Data is now emerging to suggest that although both IKK-1 and IKK-2 associate with NIK, they are differentially activated, and therefore might represent an important integration point for the spectrum of signals that activate NF-κB. Importantly, MEKK-1 (one of the components of the putative signalosome and a target for UV light, LPS induced signalling molecules and small GTPases) has been found to activate IKK-2 but not IKK-1. Similarly, NIK phosphorylation of IKK-1 results in a dramatic increase in IKK-1 activity but only a small effect on IKK-2 (for review, see Mercurio, F., and Manning, A. M., Current Opinion in Cell Biology, 11:226-232, 1999).

Inhibition of NF-κB activation is likely to be of broad utility in the treatment of inflammatory disease.

WO 98/02430 and EP 853 083 disclose various 4-pyridyl derivatives, and EP 908 456 discloses various 3-pyrazolyl derivatives.

DE 19725450 discloses various 3-pyridinyl and 5-pyrimidyl derivatives.

WO 99/46244, WO 98/54116 and EP 202 538 disclose a series of substituted thienyl compounds said to possess biological activity.

DISCLOSURE OF THE INVENTION

According to the present invention, there is provided a compound of formula (I)

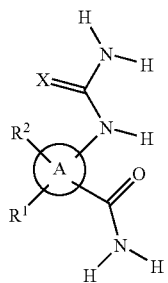

(I)

in which:

A represents a 5-membered heteroaromatic ring containing one or two heteroatoms selected independently from oxygen, nitrogen or sulfur;

$R^1$ represents a phenyl group or a 5- to 7-membered heteroaromatic ring containing one to three heteroatoms selected independently from oxygen, nitrogen or sulfur; said phenyl or heteroaromatic ring being optionally substituted by one or more substituents selected independently from halogen, cyano, nitro, —$NR^3R^4$, —$CONR^5R^6$, —$COOR^7$, —$NR^8COR^9$, —$SR^{10}$, —$S(O)_m R^{10}$, —$SO_2NR^5R^6$, —$NR^8SO_2R^{10}$, $C_1$-$C_6$ alkyl, trifluoromethyl, —$(CH_2)_n R^{11}$, —$O(CH_2)_n R^{11}$ or —$OR^{12}$;

$R^2$ represents hydrogen, halogen, cyano, nitro, —$NR^{13}R^{14}$, —$CONR^{15}R^{16}$, —$COOR^{17}$, —$NR^{18}COR^{19}$, —$S(O)_m R^{20}$, —$SO_2NR^{15}R^{16}$, —$NR^{18}SO_2R^{20}$, $C_1$-$C_2$ alkyl, trifluoromethyl, $C_2$-$C_3$ alkenyl, $C_2$-$C_3$ alkynyl, trifluoromethoxy, $C_1$-$C_2$ alkoxy or $C_1$-$C_2$ alkanoyl;

X represents oxygen or sulphur;

each of $R^3$, $R^4$, $R^5$, $R^6$, $R^7$, $R^8$, $R^9$, $R^{10}$ and $R^{12}$ independently represent a hydrogen atom or $C_1$-$C_6$ alkyl;

$R^{11}$ represents $NR^{21}R^{22}$ where $R^{21}$ and $R^{22}$ are independently hydrogen or $C_1$-$C_6$ alkyl optionally substituted by $C_1$-$C_4$ alkoxy; or $R^{21}$ and $R^{22}$ together with the nitrogen atom to which they are attached form a 5- or 6-membered saturated ring optionally containing a further O, S or $NR^{23}$ group where $R^{23}$ is hydrogen or $C_1$-$C_6$ alkyl; or $R^{11}$ represents $OR^{24}$ where $R^{24}$ represents $C_1$-C6 alkyl;

each of $R^{13}$, $R^{14}$, $R^{15}$, $R^{16}$, $R^{17}$, $R^{18}$, $R^{19}$ and $R^{20}$ independently represent a hydrogen atom or $C_1$-$C_2$ alkyl;

m represents an integer 0, 1 or 2;

n represents an integer 2, 3 or 4;

and optical isomers, racemates and tautomers thereof and pharmaceutically acceptable salts or solvates thereof:

provided that:

when A represents thiophene, furan or pyrrole, then $R^1$ is not 4-pyridinyl or 3-pyrazolyl; and when A represents oxazole, thiazole or imidazole, then $R^1$ is not 3-pyridinyl or 5-pyrimidyl.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

Preferably, X represents oxygen.

The compounds of formula (I) and their pharmaceutically acceptable salts, enantiomers and racemates have the advantage that they are inhibitors of the enzyme IKK2.

The invention further provides a process for the preparation of compounds of formula (I) or a pharmaceutically acceptable salt, enantiomer or racemate thereof.

According to the invention there is also provided a compound of formula (I), or a pharmaceutically acceptable salt, enantiomer or racemate thereof, for use as a medicament.

Another aspect of the invention provides the use of a compound of formula (I) or a pharmaceutically acceptable salt, enantiomer or racemate thereof, in the manufacture of a medicament, for the treatment or prophylaxis of diseases or conditions in which inhibition of IKK2 activity is beneficial.

A more particular aspect of the invention provides the use of a compound of formula (I) or a pharmaceutically acceptable salt, enantiomer or racemate thereof, in the manufacture of a medicament, for the treatment or prophylaxis of inflammatory disease.

According to the invention, there is also provided a method of treating, or reducing the risk of, diseases or conditions in which inhibition of IKK2 activity is beneficial which comprises administering to a person suffering from or at risk of, said disease or condition, a therapeutically effective amount of a compound of formula (I), or a pharmaceutically acceptable salt, enantiomer or racemate thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt, enantiomer or racemate thereof.

In formula (I) the group A is a 5-membered heteroaromatic ring containing one or two heteroatoms selected independently from oxygen, nitrogen or sulfur. Preferably A is substituted as shown below in formula (Ia) where B and D are selected from $CR^2$, S, O and $NR^{25}$ where $R^{25}$ is hydrogen or $C_1$-$C_6$ alkyl:

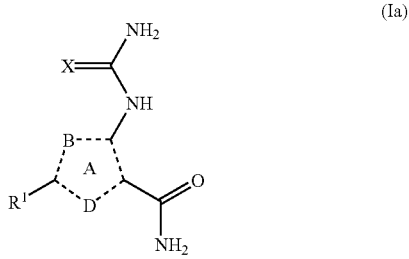

(Ia)

Preferred A groups include thiophene, furan, pyrrole, imidazole, thiazole and oxazole. It is particularly preferred that ring A represents thiophene.

Suitably the group $R^1$ is a phenyl or a 5- to 7-membered heteroaromatic ring containing one to three heteroatoms selected independently from oxygen, nitrogen or sulfur; said phenyl or heteroaromatic ring being optionally substituted by one or more substituents selected from halogen, cyano, nitro, —$NR^3R^4$, —$CONR^5R^6$, —$COOR^7$, —$NR^8COR^9$, —$SR^{10}$, —$S(O)_m R^{10}$, —$SO_2NR^5R^6$, —$NR^8SO_2R^{10}$, $C_1$-$C_6$ alkyl, trifluoromethyl, —$(CH_2)_n R^{11}$, —$O(CH_2)_n R^{11}$ or —$OR^{12}$. Preferred substituents are halogen, cyano, —$NR^3R^4$, —$SO_2R^{10}$, trifluoromethyl, —$O(CH_2)_n R^{11}$ or —$OR^{12}$. In one preferred embodiment, $R^1$ represents optionally substituted phenyl. In another preferred embodiment, $R^1$ represents an optionally substituted 5- or 6-membered heteroaromatic ring containing one or two heteroatoms selected independently from oxygen, nitrogen or sulfur.

When $R^{11}$ is $NR^{21}R^{22}$ and $R^{21}$ and $R^{22}$ together with the nitrogen atom to which they are attached form a 5- or 6-membered saturated ring, preferred examples of such rings include morpholine, pyrrolidine and piperidine rings. When $R^{11}$ is $NR^{21}R^{22}$ and $R^{21}$ and $R^{22}$ are alkyl, these alkyl groups are preferably methyl.

Particularly advantageous compounds of formula (I) are those in which $R^1$ represents optionally substituted phenyl. More preferably $R^1$ represents phenyl or phenyl substituted by halogen, methoxy, hydroxy, $OCH_2CH_2NMe_2$, $OCH_2CH_2CH_2NMe_2$, morphinolylethoxy, pyrrolidinylethoxy and piperidylethoxy.

It is preferred that the group $R^2$ in formula (I) represents H, halogen or $C_1$-$C_2$ alkyl. It is more preferred that the group $R^2$ represents H or methyl. It is even more preferred that the group $R^2$ in formula (I) represents H.

Particularly preferred compounds of the invention include those exemplified herein:

3-[(aminocarbonyl)amino]-5-phenyl-2-thiophenecarboxamide;
3-[(aminocarbonyl)amino]-5-(3-chlorophenyl)-2-thiophenecarboxamide;
3-[(aminocarbonyl)amino]-5-(4-fluorophenyl)-2-thiophenecarboxamide;
3-[(aminocarbonyl)amino]-5-(4-chlorophenyl)-2-thiophenecarboxamide;
3-[(aminocarbonyl)amino]-5-(4-isobutylphenyl)-2-thiophenecarboxamide;
3-[(aminocarbonyl)amino]-5-(2-thienyl)-2-thiophenecarboxamide;
3-[(aminocarbonyl)amino]-5-(4-methoxyphenyl)-2-thiophenecarboxamide;
3-[(aminocarbonyl)amino]-5-(3-thienyl)-2-thiophenecarboxamide;
3-[(aminocarbonyl)amino]-5-(3-hydroxyphenyl)-2-thiophenecarboxamide;
3-[(aminocarbonyl)amino]-5-(2-chlorophenyl)-2-thiophenecarboxamide;
3-[(aminocarbonyl)amino]-5-(2-methoxyphenyl)-2-thiophenecarboxamide;
3-[(aminocarbonyl)amino]-5-{2-[2-(dimethylamino)ethoxy]phenyl}-2-thiophenecarboxamide;
3-[(aminocarbonyl)amino]-5-{4-[2-(dimethylamino)ethoxy]phenyl}-2-thiophenecarboxamide;
3-[(aminocarbonyl)amino]-5-(3-methoxyphenyl)-2-thiophenecarboxamide;
2-[(aminocarbonyl)amino]-5-phenyl-3-thiophenecarboxamide;
3-[(aminocarbonyl)amino]-5-{4-[2-(1-morpholinyl)ethoxy]phenyl}-2-thiophenecarboxamide;
3-[(aminocarbonyl)amino]-5-{4-[2-(1-pyrrolidinyl)ethoxy]phenyl}-2-thiophenecarboxamide;
3-[(aminocarbonyl)amino]-5-{4-[2-(1-piperidinyl)ethoxy]phenyl}-2-thiophenecarboxamide;
3-[(aminocarbonyl)amino]-5-{4-[3-(dimethylamino)propoxy]phenyl}-2-thiophenecarboxamide;
3-[(aminocarbonyl)amino]-5-{3-[2-(dimethylamino)ethoxy]phenyl)}-2-thiophenecarboxamide;
3-[(aminocarbonyl)amino]-5-{3-[2-(1-morpholinyl)ethoxy]phenyl}-2-thiophenecarboxamide;
3-[(aminocarbonyl)amino]-5-{3-[2-(1-pyrrolidinyl)ethoxy]phenyl}-2-thiophenecarboxamide;
3-[(aminocarbonyl)amino]-5-{3-[2-(1-piperidinyl)ethoxy]phenyl}-2-thiophenecarboxamide;
3-[(aminocarbonyl)amino]-5-{3-[3-(dimethylamino)propoxy]phenyl}-2-thiophenecarboxamide;
3-[(aminocarbonyl)amino]-5-{2-[2-(1-morpholinyl)ethoxy]phenyl}-2-thiophenecarboxamide;
3-[(aminocarbonyl)amino]-5-{2-[2-(1-pyrrolidinyl)ethoxy]phenyl}-2-thiophenecarboxamide;
3-[(aminocarbonyl)amino]-5-{2-[2-(1-piperidinyl)ethoxy]phenyl}-2-thiophenecarboxamide;
3-[(aminocarbonyl)amino]-5-{2-[3-(dimethylamino)propoxy]phenyl}-2-thiophenecarboxamide;
2-[(aminocarbonyl)amino]-4-methyl-5-(4-chlorophenyl)-3-thiophenecarboxamide;
2-[(aminocarbonyl)amino]-4-methyl-5-(4-methylphenyl)-3-thiophenecarboxamide;
2-[(aminocarbonyl)amino]-4-ethyl-5-phenyl-3-thiophenecarboxamide;
2-[(aminocarbonyl)amino]-4-methyl-5-(4-methoxyphenyl)-3-thiophenecarboxamide;
2-[(aminocarbonyl)amino]-4-methyl-5-(4-fluorophenyl)-3-thiophenecarboxamide;
2-[(aminocarbonyl)amino]-4-methyl-5-(3-fluorophenyl)-3-thiophenecarboxamide;
2-[(aminocarbonyl)amino]-4-methyl-5-(3-methoxyphenyl)-3-thiophenecarboxamide;
2-[(aminocarbonyl)amino]-4-methyl-5-(3-chloro-4-methoxyphenyl)-3-thiophenecarboxamide;
2-[(aminocarbonyl)amino]-4-methyl-5-(2-chlorophenyl)-3-thiophenecarboxamide;
2-[(aminocarbonyl)amino]-4-methyl-5-(3-trifluoromethylphenyl)-3-thiophenecarboxamide;
2-[(aminocarbonyl)amino]-4-methyl-5-(3)-methyl-4-methoxyphenyl)-3-thiophenecarboxamide;
2-[(aminocarbonyl)amino]-4-methyl-5-(3,5-dimethoxyphenyl)-3-thiophenecarboxamide;
2-[(aminocarbonyl)amino]-4-methyl-5-(2,3-dimethoxyphenyl)-3-thiophenecarboxamide;
2-[(aminocarbonyl)amino]-4-methyl-5-(4-isopropylphenyl)-3-thiophenecarboxamide;
2-[(aminocarbonyl)amino]-4-methyl-5-(3,4,5-trimethoxyphenyl)-3-thiophenecarboxamide;
2-[(aminocarbonyl)amino]-4-methyl-5-(2-pyridyl)-3-thiophenecarboxamide;
2-[(aminocarbonyl)amino]-5-[2-(5-methoxypyridyl)]-4-methyl-3-thiophenecarboxamide;
2-[(aminocarbonyl)amino]-4-methyl-5-(4-pyrimidyl)-3-thiophenecarboxamide;
2-[(aminocarbonyl)amino]-4-methyl-5-(2-pyrazinyl)-3-thiophenecarboxamide;
2-[(aminocarbonyl)amino]-4-methyl-5-(3,4-dichlorophenyl)-3-thiophenecarboxamide;
2-[(aminocarbonyl)amino]-4-methyl-5-(4-cyanophenyl)-3-thiophenecarboxamide;
2-[(aminocarbonyl)amino]-4-methyl-5-(4-hydroxyphenyl)-3-thiophenecarboxamide;
2-[(aminocarbonyl)amino]-4-methyl-5-(4-[2-(1-piperidinyl)ethoxy]phenyl)-3-thiophenecarboxamide;
2-[(aminocarbonyl)amino]-4-methyl-5-(4-[2-(diethylamino)ethoxy]phenyl)-3-thiophenecarboxamide;
2-[(aminocarbonyl)amino]-4-methyl-5-(2-furyl)-3-thiophenecarboxamide;
2-[(aminocarbonyl)amino]-4-trifluoromethyl-5-phenyl-3-thiophenecarboxamide;
2-[(aminocarbonyl)amino]-4-methyl-5-(2-(4-methylthiazolyl))-3-thiophenecarboxamide;
2-[(aminocarbonyl)amino]-4-methyl-5-phenyl-3-thiophenecarboxamide;

2-[(aminocarbonyl)amino]-4-methyl-5-(3-methyl-isoxazol-5-yl)-3-thiophenecarboxamide;
2-[(aminocarbonyl)amino]-5-(4-cyanophenyl)-3-thiophenecarboxamide;
2-[(aminocarbonyl)amino]-5-(4-trifluoromethylphenyl)-3-thiophenecarboxamide;
2-[(aminocarbonyl)amino]-5-(2,4-difluorophenyl)-3-thiophenecarboxamide;
2-[(aminocarbonyl)amino]-5-(2-pyridyl)-3-thiophenecarboxamide;
2-[(aminocarbonyl)amino]-5-(3-pyridyl)-3-thiophenecarboxamide;
2-[(aminocarbonyl)amino]-5-[5-(2-methoxypyridyl]-3-thiophenecarboxamide;
2-[(aminocarbonyl)amino]-5-[5-(2,4-dimethoxypyrimidyl)]-3-thiophenecarboxamide;
2-[(aminocarbonyl)amino]-5-(4-hydroxyphenyl)-3-thiophenecarboxamide;
2-[(aminocarbonyl)amino]-5-(4-chlorophenyl)-3-thiophenecarboxamide;
2-[(aminocarbonyl)amino]-5-(4-methanesulphonylphenyl)-3-thiophenecarboxamide;
2-[(aminocarbonyl)amino]-5-(2-(N-t-butoxycarbonyl)pyrrolyl)-3-thiophenecarboxamide;
2-[(aminocarbonyl)amino]-5-(2-(5-cyanothienyl))-3-thiophenecarboxamide;
2-[(aminocarbonyl)amino]-5-(3,5-dimethyl-isoxazol-4-yl)-3-thiophenecarboxamide;
2-[(aminocarbonyl)amino]-5-(3-furyl)-3-thiophenecarboxamide;
2-[(aminocarbonyl)amino]-5-(2-pyrrolyl)-3-thiophenecarboxamide;
2-[(aminocarbonyl)amino]-5-(5-pyrimidinyl)-3-thiophenecarboxamide;
2-[(aminocarbonyl)amino]-5-(2-(5-chlorothienyl))-3-thiophenecarboxamide;
2-[(aminocarbonyl)amino]-5-[2-(5-trifluoromethylpyridyl)]-3-thiophenecarboxamide;
2-[(aminocarbonyl)amino]-5-[2-(5-bromopyridyl)]-3-thiophenecarboxamide;
2-[(aminocarbonyl)amino]-5-(2-(5-cyanofuryl))-3-thiophenecarboxamide;
2-[(aminocarbonyl)amino]-5-(4-[2-(1-piperidinyl)ethoxy]phenyl)-3-thiophenecarboxamide;
2-[(aminocarbonyl)amino]-5-(4-[2-(1-(2,2,6,6-tetramethyl)piperidinyl)ethoxy]phenyl)-3-thiophenecarboxamide;
2-[(aminocarbonyl)amino]-5-(4-(thiazol-4-yl-methoxy)phenyl)-3-thiophenecarboxamide;
2-[(aminocarbonyl)amino]-5-(4-[2-(dimethylamino)ethoxy]phenyl)-3-thiophenecarboxamide;
2-[(aminocarbonyl)amino]-5-(4-[2-(diethylamino)ethoxy]phenyl)-3-thiophenecarboxamide;
2-[(aminocarbonyl)amino]-5-(4-[2-(1-morpholinyl)ethoxy]phenyl)-3-thiophenecarboxamide;
2-[(aminocarbonyl)amino]-5-(2-furyl)-3-thiophenecarboxamide;
2-[(aminocarbonyl)amino]-5-(2-(5-methylfuryl))-3-thiophenecarboxamide;
5-[(aminocarbonyl)amino]-2-(3,5-dichlorophenyl)-1,3-oxazole-4-carboxamide;
5-[(aminocarbonyl)amino]-2-(4-trifluoromethylphenyl)-1,3-oxazole-4-carboxamide;
2-[(aminothiocarbonyl)amino-5-phenyl-3-thiophenecarboxamide;

and pharmaceutically acceptable salts and solvates thereof.

Unless otherwise indicated, the term "$C_1$-$C_6$ alkyl" referred to herein denotes a straight or branched chain alkyl group having from 1 to 6 carbon atoms. Examples of such groups include methyl, ethyl, n-propyl, i-propyl, n-butyl, i-butyl and t-butyl. The term "$C_1$-$C_2$ alkyl" is to be interpreted analogously.

Unless otherwise indicated, the term "$C_2$-$C_3$ alkenyl" referred to herein denotes a straight or branched chain alkyl group having 2 or 3 carbon atoms incorporating at least one carbon-carbon double bond. Examples of such groups include ethenyl and propenyl.

Unless otherwise indicated, the term "$C_2$-$C_3$ alkynyl" referred to herein denotes a straight chain alkyl group having 2 or 3 carbon atoms incorporating one carbon-carbon triple bond. Examples of such groups include ethynyl and propynyl.

Unless otherwise indicated, the term "$C_1$-$C_4$ alkoxy" referred to herein denotes a straight or branched chain alkoxy group having 1 to 4 carbon atoms. Examples of such groups include methoxy, ethoxy and isopropoxy. The term "$C_1$-$C_2$ alkoxy" is to be interpreted analogously.

Unless otherwise indicated, the term "$C_1$-$C_2$ alkanoyl" referred to herein denotes a formyl or acetyl group.

Unless otherwise indicated, the term "halogen" referred to herein denotes fluoro, chloro, bromo and iodo.

Examples of a 5- to 7-membered heteroaromatic ring containing one to three heteroatoms selected independently from oxygen, nitrogen or sulfur include furan, thiophene, pyrrole, oxazole, isoxazole, thiazole, isothiazole, imidazole, pyrazole, triazole, pyridine, pyridazine pyrimidine and pyrazine.

According to the invention there is also provided a process for the preparation of a compound of formula (I) or a pharmaceutically acceptable salt, enantiomer or racemate thereof which comprises:

(a) reaction of a compound of formula (II):

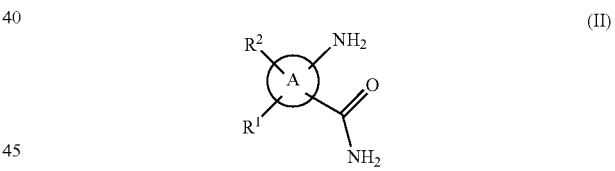

wherein A, $R^1$ and $R^2$ are as defined in formula (I) with an isocyanate (X=O) or an isothiocyanate (X=S); or (b) reaction of compound of formula (III) with a compound of formula (IV)

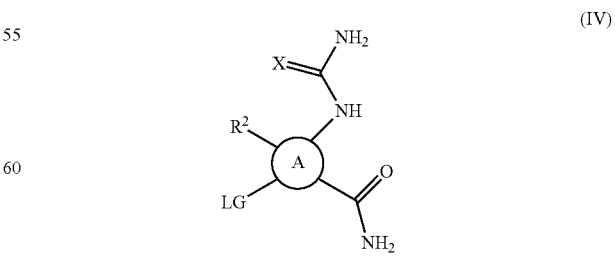

wherein A, X, $R^1$ and $R^2$ are as defined in formula (I) and LG represents a leaving, group; or (c) reaction of compound of formula (V) with a compound of formula (VI)

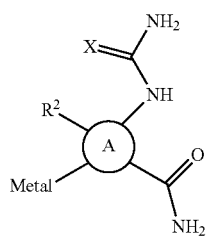

wherein A, X, R$^1$ and R$^2$ are as defined in formula (I) and LG represents a leaving, group;

and where necessary converting the resultant compound of formula (I), or another salt thereof, into a pharmaceutically acceptable salt thereof, or converting the resultant compound of formula (I) into a further compound of formula (I); and where desired converting the resultant compound of formula (I) into an optical isomer thereof.

In process (a), suitable isocyanate reagents include trimethylsilylisocyanate, trimethylsilylisothiocyanate, chlorosulphonylisocyanate, trichloroacetylisocyanate and sodium isocyanate. The reaction with trimethylsilylisocyanate or trimethylsilylisothiocyanate can be carried out in a solvent such as dichloromethane/dimethylformamide at a suitable elevated temperature, for example, at the reflux temperature of the reaction mixture. The reaction with chlorosulphonylisocyanate can be carried out in a solvent such as toluene at ambient temperature. The reaction with sodium isocyanate can be carried out in a suitable solvent system such as aqueous acetic acid at ambient temperature. The trichloroacetyhisocyanate reaction can be carried out in a suitable solvent system such as acetonitrile at ambient temperature, and subsequently treating the mixture with ammonia to give compounds of the general formula (I).

In processes (b) and (c), the compounds of formulae (III) and (IV) or of formulae (V) and (VI) are reacted together under catalysis provided by a complex of a transition metal such as palladium or nickel. In compounds of formulae (III) and (VI), under appropriate conditions, "metal" can be a metal or semi-metal such as magnesium, zinc, copper, tin, silicon, zirconium, aluminium or boron. Suitable leaving groups include iodo, bromo, chloro, triflate or phosphonate.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula (I) may involve, at an appropriate stage, the addition and removal of one or more protecting groups.

The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Greene & P. G. M. Wuts, Wiley-Interscience (1991).

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt. enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying. The reaction may also be a metathetical process or it may be carried out on an ion exchange resin.

Compounds of formula (II) can be prepared by standard chemistry described in the lo literature [for example, J. Het. Chem. 36, 333(1999)] or by reaction of compounds of formula (VII):

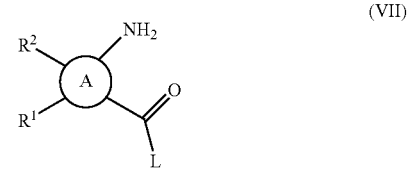

where A, R$^1$ and R$^2$ are as defined in formula (I), and L represents a leaving group, with ammonia. Suitable groups L include halogen, in particular chloro.

Compounds of formula (VII) where L is halo can be prepared from the corresponding compound of formula (VIII):

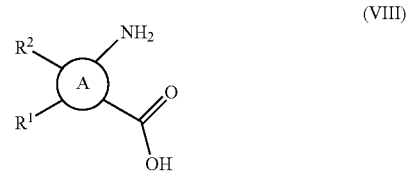

where A, R$^1$ and R$^2$ are as defined in formula (I), by treating with a halogenating agent such as thionyl chloride.

Compounds of formulae (III), (IV), (V), (VI) and (VIII) are commercially available or can be prepared using standard chemistry as exemplified herein.

Certain novel intermediate compounds form a further aspect of the invention.

The compounds of formula (I) have activity as pharmaceuticals, in particular as IKK2 enzyme inhibitors, and may be used in the treatment (therapeutic or prophylactic) of conditions/diseases in human and non-human animals in which inhibition of IKK2 is beneficial. Examples of such conditions/diseases include inflammatory diseases or diseases with an inflammatory component. Particular diseases include inflammatory arthritides including rheumatoid arthritis, osteoarthritis, spondylitis, Reiters syndrome. psoriatic arthritis, lupus and bone resorptive disease: multiple sclerosis. inflammatory bowel disease including Crohn's disease; asthma, chronic obstructive pulmonary disease, emphysema, rhinitis, myasthenia gravis, Graves' disease, allograft rejection, psoriasis, dermatitis, allergic disorders, immune complex diseases, cachexia, ARDS, toxic shock, cardiovascular disorders, heart failure, myocardial infarcts, atherosclerosis, reperfusion injury, AIDS and cancer.

Thus, the present invention provides a compound of formula (I), or a pharmaceutically acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of diseases or conditions in which modulation of the IKK2 enzyme activity is beneficial.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention still further provides a method of treating an IKK2 mediated disease which comprises administering to a patient a therapeutically effective amount of a compound of formula (I), or a pharmaceutically acceptable salt or solvate thereof, as hereinbefore defined.

The invention also provides a method of treating an inflammatory disease, especially asthma, rheumatoid arthritis or multiple sclerosis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Conventional procedures for the selection and preparation of suitable pharmaceutical formulations are described in, for example, "Pharmaceuticals—The Science of Dosage Form Designs", M. E. Aulton, Churchill Livingstone, 1988.

The invention is illustrated, but in no way limited, by the following examples:

EXAMPLE 1

3-[(Aminocarbonyl)amino]-5-phenyl-2-thiophenecarboxamide

3-Amino-5-phenyl-2-thiophenecarboxamide (0.5 g), trimethylsilylisocyanate (3 mL), dichloromethane (15 mL) and dimethylformamide (3 mL) were heated at reflux for 3 days. The reaction mixture was cooled and the resulting solid was filtered off, washed with methanol and then ether to give the title urea (0.39 g).

m.p.>300° C. $^1$H NMR (DMSO-D6) 10.06 (1H, s), 8.25 (1H, s), 7.62 (2H, d), 7.50-7.37 (5H, m). 6.63 (2H, s).

EXAMPLE 2

3-[(Aminocarbonyl)amino]-5-(3-chlorophenyl)-2-thiophenecarboxamide a) Methyl 3-amino-5-(3-chlorophenyl)-2-thiophenecarboxylate Phosphorous oxychloride (6.7 mL) was added to dimethylformamide (11 mL) with ice cooling to keep the internal temperature below 25° C. After 20 minutes, (3-chlorophenyl)ethanone (5 g) was added portionwise keeping the internal temperature below 30° C. The reaction mixture was heated to 50° C. and then treated cautiously with hydroxylamine hydrochloride (10 g). The reaction mixture was stirred for 20 minutes at room temperature and water (50 mL) was added. After a further 30 minutes, the reaction mixture was extracted three times with ethyl acetate. The combined extracts were washed with brine, dried (MgSO$_4$) and evaporated to give an oil. This oil was dissolved in methanol (50 mL) and treated with methyl mercaptoacetate (2.7 mL) and sodium methoxide (7.3 mL of a 25% solution in methanol). After reflux for 1 h, the cooled reaction mixture was reduced to one third volume and water was added. The reaction mixture was extracted three times with ethyl acetate. The combined extracts were dried (MgSO$_4$), the solvent was evaporated and the residue was chromatographed on silica eluting with dichloromethane/isohexane mixtures to give the sub-title ester (2.0 g).

m.p. 105-6° C. MS (EI) 267 (M)$^-$. $^1$H NMR (DMSO-D6) 7.68 (1H, s); 7.60 (1H, m); 7.48 (2H, m); 7.02 (1H, s); 6.60 (2H, s); 3.74 (3H, s).

b) 3-Amino-5-(3-chlorophenyl)-2-thiophenecarboxylic acid

Methyl 3-amino-5-(3-chlorophenyl)-2-thiophenecarboxylate (1.0 g), 2M sodium hydroxide (2 mL) and methanol (10 mL) were heated at 70° C. for 2 days. The methanol was evaporated off and the residue was acidified with 2M hydrochloric acid. Extraction into ethyl acetate followed by drying (MgSO$_4$) and evaporation of the solvent gave the sub-title acid (0.8 g).

MS (APCI) 252 (M+H)$^-$. $^1$H NMR (DMSO-D6) 7.62 (1H, d); 7.60 (1H, m); 7.43 (2H, m); 7.02 (1H, s).

c) 3-Amino-5-(3-chlorophenyl)-2-thiophenecarboxamide

3-Amino-5-(3-chlorophenyl)-2-thiophenecarboxylic acid (0.8 g) and thionyl chloride (20 mL) were heated at reflux for 1 h. After cooling, the excess thionyl chloride was evaporated off and final traces were removed by azeotroping with toluene. The residue was dissolved in acetonitrile (50 mL) and ammonia (d 0.88, 10 mL) was added. After stirring for 1 h, the solvent was evaporated and the residue chromatographed on silica eluting with ethyl acetate/dichloromethane mixtures. Trituration with ether gave the sub-title amide (0.48 g).

m.p. 164-5° C. MS (APCI) 253 (M+H)$^-$. $^1$H NMR (DMSO-D6) 7.62 (1H, d); 7.55 (1H, dd); 7.45 (2H, m); 7.02 (1H, s); 6.98 (2H, s); 6.50 (2H, s).

d) 3-[(Aminocarbonyl)amino]-5-(3-chlorophenyl)-2-thiophenecarboxamide

Prepared by the method of Example 1 from 3-amino-5-(3-chlorophenyl)-2-thiophenecarboxamide and trimethylsilylisocyanate.

m.p.>300° C. MS (APCI) 253 (M+H)$^-$. $^1$H NMR (DMSO-D6) 10.03 (1H, s); 8.30 (1H, s); 7.62 (1H, d); 7.60-7.40 (4H, m); 7.30-7.00 (1H, m); 6.70 (2H, s).

EXAMPLE 3

3-[(Aminocarbonyl)amino]-5-(4-fluorophenyl)-2-thiophenecarboxamide

Sodium isocyanate (1.08 g) was added portionwise to a stirred suspension of 3-amino-5-(4-fluorophenyl)-2-thiophenecarboxamide (3.2 g) in acetic acid (150 mL) and water (90 mL). After 20 h, the solid was filtered off and washed with water, methanol and ether. Recrystallisation from methanol/dimethylsulphoxide gave the title urea (0.5 g) as a 1:1 dimethylsulphoxide solvate.

m.p.>320° C. MS (APCI) 278 (M-H)$^+$. $^1$H NMR (DMSO-D6) 10.07 (1H, s); 8.22 (1H, s); 7.67 (2H, t); 7.40 (2H, s); 7.29 (2H, t); 6.65 (2H, s).

EXAMPLE 3a

3-[(Aminocarbonyl)amino]-5-(4-chlorophenyl)-2-thiophenecarboxamide

Prepared by the method of Example 3 from 3-amino-5-(4-chlorophenyl)-2-thiophenecarboxamide.

MS (ES) 296 (M+H)$^-$. $^1$H NMR (DMSO-D6) 11.03 (1H, s), 8.2 (1H, s), 7.6 (2H, d), 7.5 (2H, d), 7.4 (2H, s), 6.8 (2H, s).

EXAMPLE 3b

3-[(Aminocarbonyl)amino]-5-(4-isobutylphenyl)-2-thiophenecarboxamide

Prepared by the method of Example 3 from 3-amino-5-(4-isobutylphenyl)-2-thiophenecarboxamide.

MS (ES) 318 (M+H)$^+$. $^1$H NMR (DMSO-D6) 11.03 (1H, s), 8.2 (1H, s), 7.5 (2H, m), 7.4 (2H, s), 7.2 (2H, m),6.6 (2H, s), 2.4 (1H, m), 1.8 (2H, m), 0.8 (6H, m).

EXAMPLE 3c

3-[(Aminocarbonyl)amino]-5-(2-thienyl)-2-thiophenecarboxamide

Prepared by the method of Example 3 from 3-amino-5-(2-thienyl)-2-thiophenecarboxamide.

MS (ES) 266 (M–H)$^-$. $^1$H NMR (DMSO-D6) 10.03 (1H, s), 8.05 (1H, s), 7.6 (1H, d), 7.4 (3H, m), 7.1 (1H, t), 6.6 (2H, s).

EXAMPLE 4

3-[(Aminocarbonyl)amino]-5-(4-methoxyphenyl)-2-thiophenecarboxamide

Prepared by the method of Example 1 from 3-amino-5-(4-methoxyphenyl)-2-thiophenecarboxamide and trimethylsilylisocyanate.

m.p.>300° C. MS (APCI) 292 (M+H)$^+$. $^1$H NMR (DMSO-D6) 10.06 (1H, s); 8.12 (1H, s); 7.55 (2H, d); 7.37 (2H, s); 7.03 (2H, d); 6.61 (2H, s); 3.80 (3H, s).

EXAMPLE 5

3-[(Aminocarbonyl)amino]-5-(3-thienyl)-2-thiophenecarboxamide

Prepared by the method of Example 1 from 3-amino-5-(3-thienyl)-2-thiophenecarboxamide and trimethylsilylisocyanate.

$^1$H NMR (DMSO-D6) 10.0 (1H, s), 8.05 (1H, s), 7.8 (1H, d), 7.65 (1H, m), (7.4 (3H, m), 6.6 (2H, s).

EXAMPLE 6

3-[(Aminocarbonyl)amino]-5-(3-hydroxyphenyl)-2-thiophenecarboxamide

3-Amino-5-(3-methoxyphenyl)-2-thiophenecarboxamide (0.5 g), trimethylsilylisocyanate (2 mL), dimethylformamide (2 mL) and dichloromethane were heated at reflux for 3 days. After cooling the solid was filtered off, suspended in dichloromethane (100 mL) and treated with boron tribromide (5 mL of a 1M solution in dichloromethane). After 3 days. methanol (50 mL) was added. After 1 h, the solvent was evaporated and the residue was triturated with 2M hydrochloric acid. The title urea was filtered off (0.35 g).

m.p.>300° C. MS (APCI) 278 (M+H)$^-$. $^1$H NMR (DMSO-D6) 10.05 (1H, s); 9.71 (1H, s); 8.19 (1H, s); 7.41 (2H, m); 7.26 (1H, t); 7.03 (2H, m); 6.79 (1H, dd); 6.62 (2H, s).

EXAMPLE 7

3-[(Aminocarbonyl)amino]5-(2-chlorophenyl)-2-thiophenecarboxamide a) 3-Amino-5-(2-chloroohenyl)-2-thiophenecarboxylic acid Prepared by the method of Example 2(b) from methyl 3-amino-5-(2-chlorophenyl)-2-thiophenecarboxylate.

MS (APCI) 252 (M+H)$^-$. $^1$H NMR (DMSO-D6) 7.60 (2H, m); 7.40 (2H, m); 6.92 (1H, s).

b) 3-Amino-5-(2-chlorophenyl)-2-thiophenecarboxamide

Prepared by the method of Example 2(c) from 3-amino-5-(2-chlorophenyl)-2-thiophenecarboxylic acid.

m.p. 87-89° C. MS (APCI) 253 (M+H)⁻. $^1$H NMR (DMSO-D6) 7.60 (2H, m); 7.40 (2H, m); 7.00 (2H, s); 6.90 (1H, s); 6.42 (2H, s).

c) 3-[(Aminocarbonyl)amino]-5-(2-chlorophenyl)-2-thiophenecarboxamide

Prepared by the method of Example 1 from 3-amino-5-(2-chlorophenyl)-2-thiophenecarboxamide and trimethylsilylisocynate.

m.p.>300° C. MS (APCI) 296 (M+H)⁻. $^1$H NMR (DMSO-D6) 7.34 (2H, s); 6.80 (2H, m); 6.70 (2H, m); 6.52 (4H, m).

EXAMPLE 8

3-[(Aminocarbonyl)amino]-5-(2-methoxyphenyl)-2-thiophenecarboxamide a) Methyl 3-amino-5-(2-methoxyphenyl)-2-thiophenecarboxylate Prepared by the method of Example 2(a) from (2-methoxyphenyl)ethanone.

m.p. 119-20° C. MS (APCI) 264 (M+H)⁺. $^1$H NMR (DMSO-D6) 7.62 (1H, dd); 7.40 (1H, t); 7.18 (1H, d); 7.05 (1H, s); 7.02 (1H, t); 6.45 (2H, s); 3.95 (3H, s); 3.75 (3H, s).

b) 3-Amino-5-(2-methoxyphenyl)-2-thiophenecarboxylic acid

Prepared by the method of Example 2(b) from methyl 3-amino-5-(2-methoxyphenyl)-2-thiophenecarboxylate and used directly for step (c).

c) 3-Amino-5-(2-methoxyphenyl)-2-thiophenecarboxamide

Prepared by the method of Example 2(c) from 3-amino-5-(2-methoxyphenyl)-2-thiophenecarboxylic acid and used directly for step (d).

d) 3-[(Aminocarbonyl)amino]-5-(2-methoxyphenyl)-2-thiophenecarboxamide

Prepared by the method of Example 1 from 3-amino-5-(2-methoxyphenyl)-2-thiophenecarboxamide and trimethylsilyllisocyanate.

m.p.>300° C. $^1$H NMR (DMSO-D6) 10.01 (1H, s); 8.33 (1H, s); 7.62 (1H, dd); 7.40-7.00 (5H, m); 6.57 (2H, s); 3.90 (3H, s).

EXAMPLE 9

3-[(Aminocarbonyl)amino]-5-{2-[2-(dimethylamino)ethoxy]phenyl}-2-thiophenecarboxamide a) 3-[(Aminocarbonyl)amino]-5-(2-hydroxyphenyl)-2-thiophenecarboxamide 3-[(Aminocarbonyl)amino]-5-(2-methoxyphenyl)-2-thiophenecarboxamide (0.1 g), boron tribromide (2 ml of a 1M solution in dichloromethane) and dichloromethane (10 mL) were stirred at room temperature for 16 h. Methanol (5 mL) was added and after 1 h, the solvent was evaporated. 2M Hydrochloric acid (10 mL) was added and, after stirring for 1 h, the phenol was filtered off and used directly in step (b).

b) 3-[(Aminocarbonyl)amino]-5-{2-[2-(dimethylamino)ethoxy]phenyl}-2-thiophenecarboxamide The phenol (0.05 g), potassium carbonate (0.05 g) and (2-chloroethyl)dimethylamine hydrochloride (0.03 g)in dimethylformamide (2 mL) were stirred at 80° C. for 24 h. The cooled reaction was poured onto ethyl acetate and brine. The aqueous layer was separated and washed twice with ethyl acetate. The combined organic extracts were washed with brine, dried (MgSO₄) and the solvent was evaporated. Chromatography on silica eluting, with dichloromethane/methanol mixtures gave the title compound (6 mg).

m.p. 180° C. MS (APCI) 349 (M+H)⁺. $^1$H NMR (DMSO-D6) 10.00 (1H, s); 8.40 (1H, s); 7.62 (1H, dd); 7.38 (3H, m); 7.20 (1H, d); 7.05 (1H, t); 6.60 (2H, s); 4.20 (2H, t); 2.80 (2H, t); 2.50 (6H, s).

EXAMPLE 10

3-[(Aminocarbonyl)amino]-5-{4-[2-(dimethylamino)ethoxy]phenyl}-2-thiophenecarboxamide a) 3-[(Aminocarbonyl)amino]-5-(4-hydroxyphenyl)-2-thiophenecarboxamide Prepared by the method of Example 6 from 3-amino-5-(4-methoxyphenyl)-2-thiophenecarboxamide and used directly in step (b).

b) 3-[(Aminocarbonyl)amino]-5-{4-[2-(dimethylamino)ethoxy]phenyl}-2-thiophenecarboxamide Prepared by the method of Example 9(b) from 3-[(aminocarbonyl)amino]-5-(4-hydroxyphenyl)-2-thiophenecarboxamide.

m.p.>300° C. MS (APCI) 349 (M+H)⁻. $^1$H NMR (DMSO-D6) 10.06 (1H, s); 8.12 (1H, s); 7.53 (2H, d); 7.40 (2H, s); 7.00 (2H, d); 6.60 (2H, s); 4.10 (2H, t); 2.60 (2H, t); 2.20 (6H, s).

EXAMPLE 11

3-[(Aminocarbonyl)amino]-5-(3-methoxyphenyl)-2-thiophenecarboxamide a) Methyl 3-amino-5-(3-methoxyphenyl)-2-thiophenecarboxylate Prepared by the method of Example 2(a) from (3-methoxyphenyl)ethanone.

m.p. 81-2° C. MS (APCI) 264 (M+H)⁻. $^1$H NMR (DMSO-D6) 7.40 (1H, t); 7.20 (1H, d); 7.15 (1H, m); 7.00 (2H, m); 6.60 (2H, s); 3.80 (3H, s); 3.70 (3H, s).

b) 3-Amino-5-(3-methoxyphenyl)-2-thiophenecarboxylic acid

Prepared by the method of Example 2(b) from methyl 3-amino-5-(3-methoxyphenyl)-2-thiophenecarboxylate and used directly in step (c).

c) 3-Amino-5-(3-methoxyphenyl)-2-thiophenecarboxamide

Prepared by the method of Example 2(c) from 3-amino-5-(3-methoxyphenyl)-2-thiophenecarboxylic acid.

m.p. 101-3° C. MS (APCI) 249 (M+H)⁺. $^1$H NMR (DMSO-D6) 7.35 (1H t); 7.20 (1H, d); 7.10 (1H, m); 7.00-6.90 (4H, m); 6.42 (2H, s); 3.80 (3H, s).

d) 3-[(Aminocarbonyl)amino]-5-(3-methoxyphenyl)-2-thiophenecarboxamide

Prepared by the method of Example 1 from 3-amino-5-(3-methoxyphenyl)-2-thiophenecarboxamide and trimethylsilyliocyanate.

m.p. 105-6° C. MS (EI) 267 (M)⁺. $^1$H NMR (DMSO-D6) 10.05 (1H, s); 8.23 (1H, s), 7.43 (2H, s); 7.39 (1H, t); 7.19 (1H, d); 7.10 (1H, s); 6.98 (1H, d); 6.62 (2H, s); 3.82 (3H, s).

EXAMPLE 12

2-[(Aminocarbonyl)amino]-5-phenyl-3-thiophenecarboxamide

Chlorosulphonylisocyanate (0.081 mL) was added to a stirred suspension at 0° C. of 2-amino-5-phenyl-3-thiophenecarboxamide (0.2 g) in toluene (10 mL). After stirring for 16 h at room temperature, the solvent was evaporated and the residue dissolved in acetonitrile (20 mL). 10% Sodium bicarbonate solution (2 mL) was added and the mixture was stirred for 1 h. After acidification with 2M hydrochloric acid, the solution was extracted three times with ethyl acetate. The combined extracts were dried ($MgSO_4$) and the solvent was evaporated. Chromatography on silica eluting with methanol/dichloromethane mixtures gave the title urea (0.027 g).

m.p. 395° C. MS (APCI) 262 $(M+H)^+$. $^1$H NMR (DMSO-D6) 11.01 (1H, s); 7.73 (1H, s); 7.69 (1H, s); 7.58 (1H, s); 7.54 (1H, s); 7.40 (2H, t); 7.35-7.20 (2H, m); 7.00 (2H, s).

The starting 2-amino-5-phenyl-3-thiophenecarboxamide was prepared as follows:

A solution of phenylacetaldehyde (7.2 g), sulphur (1.92 g), cyanoacetamide (5.1 g) and triethylamine (4.53 mL) in dimethylformamide (45 mL) was stirred at room temperature for 1 h. The resulting solution was added to water (300 mL) and the solid precipitate was filtered off and washed with water. The dried solid was triturated with ether and collected (5.5 g).

MS (ES) 219 $(M+H)^-$. $^1$H NMR (DMSO-D6) 7.55 (1H, s), 7.4 (2H, m), 7.35 (5H, m), 7.1 (1H, m).

EXAMPLE 13

3-[(Aminocarbonyl)amino]-5-{4-[2-(1-morpholinyl)ethoxy]phenyl}-2-thiophenecarboxamide Prepared by the method of Example 9(b) using the product of Example 10 (a) and N-(2-chloroethyl)morpholine.

MS (EI) 390 $(M)^+$.

EXAMPLE 14

3-[(Aminocarbonyl)amino]-5-{4-[2-(1-pyrrolidinyl)ethoxy]phenyl}-2-thiophenecarboxamide Prepared by the method of Example 9(b) using the product of Example 10 (a) and N-(2-chloroethyl)pyrrolidine.

MS (EI) 374 $(M)^+$.

EXAMPLE 15

3-[(Aminocarbonyl)amino]-5-{4-[2-(1-piperidinyl)ethoxy]phenyl}-2-thiophenecarboxamide Prepared by the method of Example 9(b) using the product of Example 10 (a) and N-(2-chloroethyl)piperidine.

MS (EI) 388 $(M)^+$.

EXAMPLE 16

3-[(Aminocarbonyl)amino]-5-{4-[3-(dimethylamino)propoxy]phenyl}-2-thiophenecarboxamide Prepared by the method of Example 9(b) using the product of Example 10 (a) and N-(3-chloropropyl)dimethylamine.

MS (EI) 362 $(M)^+$.

EXAMPLE 17

3-[(Aminocarbonyl)amino]-5-{3-[2-(dimethylamino)ethoxy]phenyl}-2-thiophenecarboxamide Prepared by the method of Example 9(b) using the product of Example 6 and N-(2-chloroethyl)dimethylamine.

MS (EI) 348 $(M)^+$.

EXAMPLE 18

3-[(Aminocarbonyl)amino]-5-{3-[2-(1-morpholinyl)ethoxy]phenyl}-2-thiophenecarboxamide Prepared by the method of Example 9(b) using the product of Example 6 and N-(2-chloroethyl)morpholine.

MS (EI) 390 $(M)^+$.

EXAMPLE 19

3-[(Aminocarbonyl)amino]-5-{3-[2-(1-pyrrolidinyl)ethoxy]phenyl}-2-thiophenecarboxamide Prepared by the method of Example 9(b) using the product of Example 6 and N-(2-chloroethyl)pyrrolidine.

MS (EI) 374 $(M)^+$.

EXAMPLE 20

3-[(Aminocarbonyl)amino]-5-{3-[2-(1-piperidinyl)ethoxy]phenyl}-2-thiophenecarboxamide Prepared by the method of Example 9(b) using the product of Example 6 and N-(2-chloroethyl)piperidine.

MS (EI) 388 $(M)^+$.

EXAMPLE 21

3-[(Aminocarbonyl)amino]-5-{3-[3-(dimethylamino)propoxy]phenyl}-2-thiophenecarboxamide Prepared by the method of Example 9(b) using the product of Example 6 and N-(3-chloropropyl)dimethylamine.

MS (EI) 362 $(M)^+$.

EXAMPLE 22

3-[(Aminocarbonyl)amino]-5-{2-[2-(1-morpholinyl)ethoxy]phenyl}-2-thiophenecarboxamide Prepared by the method of Example 9(b) but using N-(2-chloroethyl)morpholine.

MS (APCI) 391 $(M+H)^-$.

EXAMPLE 23

3-[(Aminocarbonyl)amino]-5-{2-[2-(1-pyrrolidinyl)ethoxy]phenyl}-2-thiophenecarboxamide Prepared by the method of Example 9(b) but using N-(2-chloroethyl)pyrrolidine.

MS (APCI) 375 $(M+H)^+$.

EXAMPLE 24

3-[(Aminocarbonyl)amino]-5-{2-[2-(1-piperidinyl)ethoxy]phenyl}-2-thiophenecarboxamide Prepared by the method of Example 9(b) but using N-(2-chloroethyl)piperidine.
MS (APCI) 389 (M+H)$^+$.

EXAMPLE 25

3-[(Aminocarbonyl)amino]-5-{2-[3-(dimethylamino)propoxy]phenyl}-2-thiophenecarboxamide Prepared by the method of Example 9(b) but using N-(3-chloropropyl)dimethylamine.
MS (APCI) 363 (M+H)$^+$.

EXAMPLE 26

2-[(Aminocarbonyl)amino]-4-methyl-5-(4-chlorophenyl)-3-thiophenecarboxamide a) 2-Amino-4-methyl-5-(4-chlorophenyl)-3-thiophencarboxamide (4-Chlorophenyl)acetone (1.7 g), cyanoacetamide (0.84 g), sulphur (0.36 g) and morpholine (1 mL) in ethanol (5 mL) were stirred and heated at 55° C. for 6 h. The reaction mixture was cooled and filtered from a small amount of insoluble material before adding to water (150 mL). The precipitated solid was filtered off, washed with water and then dried. The product was then triturated with ether and collected (1.0 g).
MS (EI) 266 (M)$^+$. $^1$H NMR (DMSO-D6) 7.4 (2H, d), 7.3 (2H, d), 6.9 (2H, s), 6.8 (2H, s), 2.2 (3H, s).

b) 2-[(Aminocarbonyl)amino]-4-methyl-5-(4-chlorophenyl)-3-thiophenecarboxamide

2-Amino-4-methyl-5-(4-chlorophenyl)-3-thiophencarboxamide (0.44 g) was suspended in acetonitrile (25 mL) and trichloroacetylisocyanate (0.2 mL) added dropwise with stirring over 10 minutes. Stirring was continued for a further 3 h at room temperature and then a 2M solution of ammonia in methanol (10 mL) was added and stirring continued for a further 2 h. The solvent was evaporated and the residue treated with water. The resultant solid was filtered off and washed with more water. The crude product was chromatographed on silica gel eluting with dichloromethane/methanol mixtures. Trituration with ether gave the title urea (0.1 g).
MS (ES) 310 (M+H)$^+$. $^1$H NMR (DMSO-D6) 10.05 (1H, s), 7.4 (2H, d), 7.35 (2H, d), 7.25 (2H, m), 6.8 (2H, s), 2.25 (3H, s).

EXAMPLE 27

2-[(Aminocarbonyl)amino]-4-methyl-5-(4-methylphenyl)-3-thiophenecarboxamide

Prepared by the method of Example 26 from (4-methylphenyl)acetone.
MS (ES) 290 (M+H)$^+$. $^1$H NMR (DMSO-D6) 10.04 (1H, m), 7.2 (6H, m), 6.7 (2H, m), 2.3 (3H, s), 2.25 (3H, s).

EXAMPLE 28

2-[(Aminocarbonyl)amino]-4-ethyl-5-phenyl-3-thiophenecarboxamide

Prepared by the method of Example 26 from 1-phenyl-2-butanone.
MS (ES) 290 (M+H)$^+$. $^1$H NMR (DMSO-D6) 9.6 (1H, m), 7.2 (7H, m), 6.6 (2H, m), 2.7 (2H, m), 1.0 (3H, t).

EXAMPLE 29

2-[(Aminocarbonyl)amino]-4-methyl-5-(4-methoxyphenyl)-3-thiophenecarboxamide

Prepared by the method of Example 26 from (4-methoxyphenyl)acetone.
MS (ES) 306 (M+H)$^-$. $^1$H NMR (DMSO-D6) 10.04 (1H, s), 7.8 (1H, m), 7.25 (3H, m), 7.0 (2H, m), 6.75 (2H, m), 3.8 (3H, s), 2.2 (3H, s).

EXAMPLE 30

2-[(Aminocarbonyl)amino]-4-methyl-5-(4-fluorophenyl)-3-thiophenecarboxamide

Prepared by the method of Example 26 from (4-fluorophenyl)acetone.
MS (ES) 294 (M+H)$^+$. $^1$H NMR (DMSO-D6) 10.05 (1H, s), 8.3 (1H, m) 7.8 (1H, m), 7.35 (2H, m), 7.2 (2H, m), 6.8 (2H, m), 2.2 (3H, s).

EXAMPLE 31

2-[(Aminocarbonyl)amino]-4-methyl-5-(3-fluorophenyl)-3-thiophenecarboxamide

Prepared by the method of Example 26 from (3-fluorophenyl)acetone.
MS (ES) 294 (M+H)$^+$. $^1$H NMR (DMSO-D6) 10.0 (1H, s), 7.4 (3H, m), 7.2 (3H, m), 6.8 (2H, s), 2.25 (3H, s).

EXAMPLE 32

2-[(Aminocarbonyl)amino]-4-methyl-5-(3-methoxyphenyl)-3-thiophenecarboxamide

Prepared by the method of Example 26 from (3-methoxyphenyl)acetone.
MS (ES) 306 (M+H)$^+$.

EXAMPLE 33

2-[(Aminocarbonyl)amino]-4-methyl-5-(3-chloro-4-methoxyphenyl)-3-thiophenecarboxamide Prepared by the method of Example 26 from (3-chloro-4-methoxyphenyl)acetone.
MS (ES) 340/342 (M+H)$^+$. $^1$H NMR (DMSO-D6) 7.25 (5H, m), 6.8 (2H, s), 3.9 (3H, s), 2.2 (3H, s).

EXAMPLE 34

2-[(Aminocarbonyl)amino]-4-methyl-5-(2-chlorophenyl)-3-thiophenecarboxamide

Prepared by the method of Example 26 from (2-chlorophenyl)acetone.

MS (ES) 310/312 (M+H)$^+$. $^1$H NMR (DMSO-D6) 10.22 (1H, s), 7.6 (1H, m), 7.4 (3H, m), 7.2 (2H, m), 6.8 (2H, s), 2.05 (3H, s).

EXAMPLE 35

2-[(Aminocarbonyl)amino]-4-methyl-5-(3-trifluoromethylphenyl)-3-thiophenecarboxamide Prepared by the method of Example 26 from (3-trifluoromethylphenyl)acetone.

MS (ES) 344 (M+H)$^-$. $^1$H NMR (DMSO-D6) 7.65 (3H, m), 7.6 (1H, s), 7.4 (2H, m), 7.2 (2H, m), 6.8 (2H, s), 2.25 (3H, s).

EXAMPLE 36

2-[(Aminocarbonyl)amino]-4-methyl-5-(3-methyl-4-methoxyphenyl)-3-thiophenecarboxamide Prepared by the method of Example 26 from (3-methyl-4-methoxyphenyl)acetone.

MS (ES) 320 (M+H)$^-$. $^1$H NMR (DMSO-D6) 10.04 (1H, m), 7.2 (1H, m), 7.1 (3H, m), 6.95 (1H, d), 6.7 (2H, s), 3.8 (3H, s), 2.2 (3H, s), 2.15 (3H, s).

EXAMPLE 37

2-[(Aminocarbonyl)amino]-4-methyl-5-(3,5-dimethoxyphenyl)-3-thiophenecarboxamide Prepared by the method of Example 26 from (3,5-dimethoxyphenyl)acetone.

MS (ES) 336 (M+H)$^-$. $^1$H NMR (DMSO-D6) 6.7 (2H, m), 6.4 (3H, s), 3.8 (6H, s), 2.25 (3H, s).

EXAMPLE 38

2-[(Aminocarbonyl)amino]-4-methyl-5-(2,3-dimethoxyphenyl)-3-thiophenecarboxamide Prepared by the method of Example 26 from (2,3-dimethoxyphenyl)acetone.

MS (ES) 336 (M+H)$^+$. $^1$H NMR (DMSO-D6) 10.16 (1H, m), 7.2(1H, m), 7.05 (3H, m), 6.8 (1H, m), 6.7 (2H, m), 3.8 (3H, s), 3.5 (3H, s), 2.1(3H, s).

EXAMPLE 39

2-[(Aminocarbonyl)amino]-4-methyl-5-(4-isopropylphenyl)-3-thiophenecarboxamide

Prepared by the method of Example 26 from (4-isopropylphenyl)acetone.

MS (ES) 316 (M–H)$^-$. $^1$H NMR (DMSO-D6) 7.25 (4H, s), 7.25 (2H, m), 6.7 (2H, m), 2.9 (1H, m), 2.25 (3H, s), 1.2 (6H, d).

EXAMPLE 40

2-[(Aminocarbonyl)amino]-4-methyl-5-(3,4,5-trimethoxyphenyl)-3-thiophenecarboxamide Prepared by the method of Example 26 from (3,4,5-trimethoxyphenyl)acetone.

MS (ES) 364 (M–H)$^-$. $^1$H NMR (DMSO-D6) 6.7 (2H, m), 6.6 (2H, s), 3.8 (6H, s),3.7 (3H, s), 2.3 (3H, s).

EXAMPLE 41

2-[(Aminocarbonyl)amino]-4-methyl-5-(4-pyridyl)-3-thiophenecarboxamide

Prepared by the method of Example 26 from (4-pyridyl)acetone.

MS (ES) 275 (M–H)$^-$. $^1$H NMR (DMSO-D6) 8.55 (2H, m), 7.2 (4H, m), 7.1 (2H, m), 2.35 (3H, s).

EXAMPLE 42

2-[(Aminocarbonyl)amino]-4-methyl-5-(2-pyridyl)-3-thiophenecarboxamide

Prepared by the method of Example 26 from (2-pyridyl)acetone.

MS (ES) 275 (M–H)$^-$. $^1$H NMR (DMSO-D6) 9.9 (1H, s) 8.5 (1H, m), 7.8 (1H, m), 7.5 (1H, m), 7.4 (2H, m), 7.2 (2H, m), 6.7 (2H, m).

a) (2-Pyridyl)acetone

2-Picoline (2 g) was dissolved in tetrahydrofuran (30 ml) and the solution was cooled to –75° C. Butyl lithium (14.73 ml. of a 1.6M-solution in hexane) was added dropwise and the mixture stirred for 2 h. Dimethylacetamide (1.87 ml) was then added dropwise and the reaction was allowed to warm up to room temperature and stirring was continued for a further 2 h. Water (8.6 ml) and 36% hydrochloric acid (1.3 ml) were added and after stirring for another 30 minutes, ethyl acetate was added. The separated solvent phase was washed with brine and then dried (MgSO$_4$). On evaporation an oil was obtained and used without further purification.

MS (ES) 134 (M–H)$^-$. $^1$H NMR (CDCl$_3$) 8.6 (1H, m), 7.6 (1H, m), 7.2 (2H, m), 3.9 (2H, s), 2.2 (3H, s).

EXAMPLE 43

2-[(Aminocarbonyl)amino]-5-[2-(5-methoxypyridyl)]-4-methyl-3-thiophenecarboxamide Prepared by the method of Example 26 from [2-(5-methoxypyridyl)]acetone.

MS (ES) 307 (M–H)$^-$. $^1$H NMR (DMSO-D6) 9.93 (1H, s), 8.26 (1H, d), 7.46-7.37 (2H, m), 7.33 (2H, bs), 6.72 (2H, bs), 3.83 (3H, s), 2.40 (3H, s).

a) [2-(5-methoxypyridyl)]acetone

Prepared in a similar manner to Example 42(a) from 3-methoxy-6-methylpyridine.

MS (ES) 166 (M+H)$^+$. $^1$H NMR (CDCl$_3$) 8.25 (1H, d), 7.22-7.10 (2H, m), 3.85 (5H, s), 2.22 (3H, s).

b) 3-Methoxy-6-methylpyridine

A solution of 3-hydroxy-6-methylpyridine (2.5 g), sodium methoxide (1.36 g) and phenyltrimethylammonium chloride (4.33 g) in dry dimethylformamide (25 ml) was heated at reflux under argon for 2.5 h. The mixture was allowed to cool then stirred at room temperature overnight. Insoluble material was removed by filtration and washed with ethanol. The filtrate was acidified with 6M hydrochloric acid and the solvent was removed in vacuo. The residue was then diluted with water, basified with 2M sodium hydroxide and extracted with ether. The combined extracts were washed with brine, dried (MgSO$_4$), filtered and evaporated. The crude product was purified by column chromatography on silica gel eluting with 3% ethyl acetate in hexane (1.55 g, 55%).

MS (ES) 124 (M+H)$^+$. $^1$H NMR (CDCl$_3$) 8.19 (1H, d), 7.10 (1H, dd), 7.05 (1H, d), 3.83 (3H, s), 2.48 (3H, s).

EXAMPLE 44

2-[(Aminocarbonyl)amino]-4-methyl-5-(4-pyrimidyl)-3-thiophenecarboxamide

Prepared by the method of Example 26 from (4-pyrimidyl)acetone.

MS (ES) 278 (M–H)$^-$. $^1$H NMR (DMSO-D6) 9.95 (1H, s), 9.00 (1H, s), 8.64 (1H, d), 7.55 (1H, d), 7.50 (2H, bs), 6.84 (2H, bs), 2.54 (3H, s).

a) (4-Pyrimidyl)acetone

4-Methylpyrimidine (2 g) was stirred in dry tetrahydrofuran (65 ml) under argon and the solution was cooled to –78° C. Lithium diisopropylamide (13.8 ml, 2M solution) was added dropwise over 20 minutes and stirring was continued at –78° C. for 1.5 h before dropwise addition of N-methoxy-N-methylacetamide (2.49 ml). The reaction mixture was stirred at –78° C. for a further 40 minutes before allowing to warm to room temperature over 1.25 h, then partitioned between saturated aqueous sodium carbonate and ethyl acetate. The layers were separated and the aqueous phase further extracted with ethyl acetate. The combined extracts were washed with brine, dried (MgSO$_4$), filtered and evaporated. The residue was purified by column chromatography on silica gel eluting with 40-50% ethyl acetate in hexane to give an oil which crystallised on standing (0.70 g, 24%).

MS (ES) 135 (M–H)$^-$. $^1$H NMR (CDCl$_3$) 14.40 (1H, s), 8.75 (1H, s), 8.35 (1H, d), 6.74 (1H, dd), 5.29 (1H, s), 2.06 (3H, s).

EXAMPLE 45

2-[(Aminocarbonyl)amino]-4-methyl-5-(2-pyrazinyl)-3-thiophenecarboxamide

Prepared by the method of Example 26 from (2-pyrazinyl)acetone.

MS (ES) 278 (M+H)$^+$. $^1$H NMR (DMSO-D6) 9.95 (1H, s), 8.76 (1H, d), 8.57 (1H, t), 8.42 (1H, d), 7.45 (2H, bs), 6.91 (2H, bs).

a) (2-Pyrazinyl)acetone

Prepared by the method of Example 44(a) from 2-methylpyrazine.

MS (ES) 135 (M–H)$^-$. $^1$H NMR (CDCl$_3$) 8.56-8.51 (2H, m), 8.48 (1H, d), 3.95 (2H, s), 2.28 (3H, s).

EXAMPLE 46

2-[(Aminocarbonyl)amino]-4-methyl-5-(3,4-dichlorophenyl)-3-thiophenecarboxamide

Prepared by the method of Example 26 from (3,4-dichlorophenyl)acetone.

MS (ES) 342 (M–H)$^-$. $^1$H NMR (DMSO-D6) 10.0 (1H, s), 8.3 (2H, m), 7.6 (1H, m), 7.35 (3H, m), 6.8 (2H, m), 2.2 (3H, s).

EXAMPLE 47

2-[(Aminocarbonyl)amino]-4-methyl-5-(4-cyanophenyl)-3-thiophenecarboxamide

Prepared by the method of Example 26 from (4-cyanophenyl)acetone.

MS (ES) 299 (M–H)$^-$.

EXAMPLE 48

2-[(Aminocarbonyl)amino]-4-methyl-5-(4-hydroxyphenyl)-3-thiophenecarboxamide

Prepared by demethylating 2-[(aminocarbonyl)amino]-4-methyl-5-(4-methoxyphenyl)-3-thiophenecarboxamide using boron tribromide as in Example 9(a).

MS (ES) 290 (M–H)$^-$. $^1$H NMR (DMSO-D6) 10.02 (1H, s), 7.8 (1H, m), 7.2 (3H, m), 7.15 (2H, m), 6.8 (2H, m), 2.2 (3H, s).

EXAMPLE 49

2-[(Aminocarbonyl)amino]-4-methyl-5-(4-[2-(1-piperidinyl)ethoxy]phenyl)-3-thiophenecarboxamide Prepared by the method of Example 26 using (4-[2-(1-piperidinyl)ethoxy]phenyl)acetone.

MS (ES) 401 (M–H)$^-$. $^1$H NMR (DMSO-D6) 10.04(1H, s), 7.25 (3H, m), 7.1 (2H, m), 6.7 (2H, m), 4.05 (2H, m), 2.6 (2H, m), 2.4 (4H, m), 2.2 (3H, s) 1.5 (4H, m), 1.4 (2H, m).

(4-[2-(1-Piperidinyl)ethoxy]phenyl)acetone was prepared as follows:—

(4-Hydroxyphenyl)acetone (1.5 g), N-chloroethylpiperidine hydrochloride (2.2 g) and potassium carbonate (3.0 g) in dimethylformamide (15 mL) were stirred and heated at 80° C. for 8 h. The reaction mixture was cooled and partitioned between ethyl acetate and water. The separated solvent phase was washed twice with saturated brine and then dried (MgSO$_4$). The resulting oil was used without further purification.

MS (ES) 262 (M+H)$^+$.

EXAMPLE 50

2-[(Aminocarbonyl)amino]-4-methyl-5-(4-[2-(diethylamino)ethoxy]phenyl)-3-thiophenecarboxamide Prepared by the method of Example 26 using (4-[2-(diethylamino)ethoxy]phenyl)acetone.

$^1$H NMR (DMSO-D6) 7.35 (3H, m), 7.15 (1H, m), 7.0 (2H, m), 6.8 (2H, m), 4.05 (2H, m) 2.8 (2H, m), 2.45 (4H, m), 2.4 (3H, s) 1.0 (6H, t).

(4-[2-(Diethylamino)ethoxy]phenyl)acetone was prepared in a similar manner to Example 49(a).

MS (ES) 249 (M+H)$^+$.

EXAMPLE 51

2-[Aminocarbonyl)amino]-4-methyl-5-(2-furyl)-3-thiophenecarboxamide

Prepared by the method of Example 26 using 1-(2-furyl)-propan-2-one.

1-(2-Furyl)-propan-2-one was prepared as follows:— a) 1-(2-Furyl)-propan-2-ol

To a solution of furan (7.93 g) in tetrahydrofuran (100 ml) cooled to 5° C. was added dropwise n-butyl lithium (80.2 ml, 1.6M in hexanes). The mixture was stirred for 2 h. A solution of propylene oxide (12.2 ml) was added dropwise and the resulting mixture was stirred at 0° C. for 1 h. The reaction mixture was quenched with saturated ammonium chloride and extracted with diethyl ether. The organics were dried (MgSO$_4$) and concentrated. The crude oil was distilled to give 1-(2-furyl)-propan-2-ol (3.85 g, b.p. 68-70° C. at 6.0 mm).

$^1$H NMR (CDCl$_3$) 7.35 (1H, d), 6.3 (1H, m), 6.1 (1H, d), 4.1 (1H, m), 2.7-2.9 (2H, m), 1.8 (1H, s), 1.2 (3H, d).

b) 1-(2-Furyl)-propan-2-one

To a solution of 1-(2-furyl)-propan-2-ol (3.25 g) in dichloromethane (200 ml) was added in one portion pyridinium chlorochromate (13.0 g). The resulting mixture was stirred at room temperature for 5 h and then filtered through a small bed of silica. The organics were evaporated to give the crude product which was used without further purification (3.53 g).

$^1$H NMR (CDCl$_3$) 7.4 (1H, d), 6.35 (1H, m), 6.2 (1H, d), 3.7 (2H, s), 2.2 (3H, s).

EXAMPLE 52

2-[(Aminocarbonyl)amino]-4-trifluoromethyl-5-phenyl-3-thiophenecarboxamide a) 2-Amino-4-trifluoromethyl-5-phenyl-3-thiophenenitrile A solution of 3,3,3-trifluoro-1-phenylpropan-2-one (1 g), malononitrile (0.39 g), sulphur (0.25 g), triethylamine (0.22 g), in ethanol (5 ml) was stirred and heated at 85° C. for 12 h. The reaction mixture was added to water (200 ml) and extracted twice into ethyl acetate (100 ml). The mixture was separated and the organic layer dried (anhydrous sodium sulfate), filtered and concentrated. The residue was chromatographed on silica gel eluting with ethyl acetate/isohexane mixtures. The solvent was removed and the product collected (0.5 g).

MS (ES) 267 (M–H)$^-$. $^1$H NMR (DMSO-D6) 7.65 (2H, s), 7.35-7.45 (5H, m).

b) 2-Amino-4-trifluoromethyl-5-phenyl-3-thiophenecarboxamide

A mixture of 2-amino-4-trifluoromethyl-5-phenyl-3-thiophenenitrile (0.12 g) and concentrated sulphuric acid (1.5 ml) was stirred and heated at 50° C. for 8 h. The reaction mixture was added to saturated aqueous sodium bicarbonate until a pH of 7 was obtained. The product was extracted into ethyl acetate (100 ml) and the organic layer was dried with anhydrous sodium sulfate (3 g), filtered and concentrated. The residue was chromatographed on silica gel eluting with ethyl acetate/isohexane mixtures. The solvent was removed and the product collected (0.07 g).

MS (ES) 285 (M–H)$^-$. $^1$H NMR (DMSO-D6) 7.35-7.45 (5H, m)), 7.2 (2H, s), 6.2 (2H, s).

c) 2-[(Aminocarbonyl)amino]-4-trifluoromethyl-5-phenyl-3-thiophenecarboxamide

2-Amino-4-trifluoromethyl-5-phenyl-3-thiophenecarboxamide (0.35 g) was suspended in tetrahydrofuran (10 ml) and trichloroacetylisocyanate (0.19 g) was added dropwise with stirring over 5 minutes. Stirring was continued for 1 h at room temperature and then a 2M solution of ammonia in methanol (10 ml) was added and stirring continued for a further 12 h. A precipitate formed and was filtered off and washed with ethyl acetate (5 ml) to give the title urea (0.12 g).

MS (ES) 328 (M–H)$^-$. $^1$H NMR (DMSO-D6) 9.2 (1H, s), 7.6 (2H, s), 7.35-7.45 (5H, m), 6.6 (2H, s).

EXAMPLE 53

2-[(Aminocarbonyl)amino]-4-methyl-5-(2-(4-methylthiazolyl))-3-thiophenecarboxamide Prepared by the method of Example 26(b) using 2-amino-4-methyl-5-(2-(4-methylthiazolyl))-3-thiophenecarboxamide.

NMR (DMSO-D6) 9.9 (1H, bs), 7.45 (2H, bs), 7.19 (1H, s), 6.85 (2H, bs), 2.49 (3H, s obscured by DMSO), 2.35 (3H, s). MS (M+H)$^+$297.3.

The preparation of the starting material was achieved as follows:

a) 2-Amino-4-methyl-5-(2-(4-methylthiazolyl))-3-thiophenecarboxamide was prepared by the method of Example 52(b) from 2-amino-3-cyano-4-methyl-5-(2-(4-methylthiazolyl))thiophene.

NMR (DMSO-D6) 7.12 (2H, s), 7.08 (1H, s), 6.97 (2H, bs), 3.27 (3H, s), 2.44 (3H, s) MS (M+H)$^+$254.

b) 2-Amino-3-cyano-4-methyl-5-(2-(4-methylthiazolyl))thiophene was prepared by the method of Example 52(a) using 1-(4-methylthiazol-2-yl)-propan-2-one.

NMR-(DMSO-D6) 7.63 (2H, s), 7.15 (1H, s), 2.26 (3H, s), 2.24 (3H, s) MS (M+H)$^+$236.

c) 1-(4-methylthiazol-2-yl)-propan-2-one

To a solution of 2,4 dimethylthiazole (2 g) in dry tetrahydrofuran (20 ml) at –70° C. under argon was added 1.6M n-butyllithium in hexanes (12 ml) dropwise, keeping the temperature below –70° C. After stirring at –60° C. for 30 minutes, N-methoxy-N-methylacetamide (1.9 ml) was added. The mixture was allowed to warm to ambient temperature and was then partitioned between water and ethyl acetate The organic phase was dried (MgSO$_4$) and the solvent removed under reduced pressure to yield a yellow oil. This was purified by column chromatography using a isohexane to 40% ethyl acetate/isohexane gradient as the eluent to yield the product as a yellow oil (630 mg, 23%).

NMR (CDCl$_3$) 6.84 (1H, s), 4.1 (2H, s), 2.44 (3H, s), 2.27 (3H, s). MS (M+H)$^-$156.

EXAMPLE 54

2-[(Aminocarbonyl)amino]-4-methyl-5-phenyl-3-thiophenecarboxamide a) 2-Cyano-3-benzyl-but-2-enoic acid amide (E/Z mixture)

A mixture of (phenyl)acetone (5 g), cyanoacetamide (3.15 g), ammonium acetate (0.29 g) and acetic acid (0.45 mL) was refluxed in toluene (50 mL) using a Dean and Stark head to remove water for 6 h. The mixture was cooled and the crystalline product was filtered off (3 g) and used without further purification.

MS (ES) 201 (M+H)+.

b) 2-Amino-4-methyl-5-phenyl-3-thiophencarboxamide

A mixture of 2-cyano-3-benzyl-but-2-enoic acid amide (E/Z mixture) (1.0 g), morpholine (0.5 mL) and sulphur (0.18 g) in ethanol (10 mL) was heated and stirred at 40° C. for 3 h. After cooling, the mixture was filtered from a trace of insoluble material and the filtrate added to water. The resulting precipitate was filtered off and washed with more water, then crystallised from 2-propanol (0.35 g).

MS (ES) 233 (M+H)+. $^1$H NMR (DMSO-D6) 7.4 (2H, m), 7.25 (3H, m), 6.9 (2H, s), 6.8 (2H, s), 2.2 (3H, s).

c) 2-[(Aminocarbonyl)amino]-4-methyl-5-phenyl-3-thiophenecarboxamide

To a mixture of 2-amino-4-methyl-5-phenyl-3-thiophencarboxamide (0.18 g) in glacial acetic acid (5 mL) and water (0.5 mL) was added sodium isocyanate (101 mg). The resulting solution was stirred at room temperature for 4 h and then poured into water. The precipitate was filtered off and washed with more water. The product was chromatographed on silica gel eluting with dichloromethane/methanol mixtures to give the title product as a solid (30 mg).

MS (ES) 276 (M+H)+. $^1$H NMR (DMSO-D6) 10.05 (1H, s), 7.4 (5H, m), 7.35 (1H, m), 6.6 (2H, s), 6.4 (2H, m), 2.4 (3H, s).

EXAMPLE 55

2-[(Aminocarbonyl)amino]-4-methyl-5-(3-methyl-isoxazol-5-yl)-3-thiophenecarboxamide Prepared by the method of Example 54 from 1-(3-methyl-isoxazol-5-yl)-propan-2-one.

MS (ES) 281 (M+H)+. $^1$H NMR (DMSO-D6) 9.95 (1H, s), 7.5 (2H, bs), 6.9 (2H, bs), 6.4 (1H, s), 2.4 (3H, s), 2.25 (3H, s).

The starting 1-(3-methyl-isoxazol-5-yl)-propan-2-one was prepared as follows:

To a solution of 3,5-dimethylisoxazole (5.28 g) in tetrahydrofuran (80 ml), cooled to −75° C., was added dropwise n-butyl lithium (37.4 ml, 1.6M solution in hexanes). After completion of the addition the mixture was stirred at −75° C. for 2 h. A solution of N-methoxy-N-methylacetamide in tetrahydrofuran (10 ml) was added dropwise over 15 minutes. The mixture was allowed to warm to room temperature and then to stir for a further 2 h. The mixture was quenched with saturated ammonium acetate and extracted with diethyl ether. The organics were combined, dried (MgSO$_4$) and concentrated. The crude product was chromatographed on silica gel eluting with a 1:1 mixture of diethyl ether/hexane to give the title compound as an oil (1.57 g).

MS (ES) 140 (M+H)+. $^1$H NMR (CDCl$_3$) 6.1 (1H, s), 3.8 (2H, s), 2.3 (3H, s), 2.2 (3H, s).

EXAMPLE 56

2-[(Aminocarbonyl)amino]-5-(4-cyanophenyl)-3-thiophenecarboxamide a) 2-Amino-3-cyanothiophene.

2,5-Dihydroxy-1,4-dithiane (14.3 g) was suspended in ethanol (250 ml) and malononitrile (13.0 g) added. The mixture was cooled to 5° C. and diethylamine (20.6 ml) in ethanol (15 ml) was added at a rate such that the temperature was maintained at 5° C. The mixture was then heated at 30-35° C. for 1.5 h. Water (280 ml) was added and the mixture poured onto crushed ice (400 g). After a short period of time pale brown crystals formed which were filtered off and dried on the filter (14.6 g).

MS (ES) 125 (M+H)+. $^1$H NMR (CDCl$_3$) 6.7 (1H, d), 6.4 (1H, d), 4.8 (2H, bs).

b) 2-Acetylamino-3-cyanothiophene

2-Amino-3-cyanothiophene (12 g) was heated at reflux in acetic anhydride (34 ml) for 15 minutes, cooled and refrigerated for 3 h. The crystalline product was filtered off (13.6 g).

MS (ES) 167 (M+H)+. $^1$H NMR (DMSO-D6) 11.6 (1H, bs), 7.1 (2H, m), 2.1 (3H, s).

c) 2-Acetylamino-5-bromo-3-cyanothiophene

2-Acetylamino-3-cyanothiophene (13.5 g) was dissolved in dimethylformamide (110 ml) and cooled in an ice/water bath. N-Bromosuccinimide (15.9 g) was added portion wise over 20 minutes and then the mixture warmed to room temperature and stirred for 3 h. The mixture was concentrated to approximately half the volume and water added to precipitate the product. This was filtered off and dried at 60° C. under vacuum (18.8 g).

$^1$H NMR (DMSO-D6) 12.0 (1H, bs), 7.4 (1H, s), 2.1 (3H, s).

d) 2-Acetylamino-3-cyano-5-(4-cyanophenyl)thiophene

2-Acetylamino-5-bromo-3-cyanothiophene (500 mg), 4-cyanophenylboronic acid (360 mg) and potassium carbonate (845 mg) were added to dimethoxyethane (15 ml) and water (2 ml) and the system purged with argon for 15 minutes. Tetrakis(triphenylphosphine)palladium(0) (236 mg) was added and the mixture heated at 80° C. for 3.25 h. The mixture was cooled, concentrated under reduced pressure to remove most of the dimethoxymethane, dichloromethane added and the mixture filtered to give the product as a pale brown solid (470 mg).

MS (ES) 266 (M−H)−. $^1$H NMR (DMSO-D6) 7.8 (5H, m), 2.1 (3H, s).

e) 2-Amino-5-(4-cyanophenyl)-3-thiophenecarboxamide

2-Acetylamino-3-cyano-5-(4-cyanophenyl)thiophene (470 mg) was heated at reflux in ethanol (15 ml) and concentrated sulphuric acid (1.5 ml) for 2.5 h. The reaction mixture was cooled and concentrated under reduced pressure. The residue was basified with 2N sodium hydroxide, with cooling, and the product was filtered off and dried (360 mg).

MS (ES) 242 (M−H)−. $^1$H NMR (DMSO-D6) 7.8 (1H, s), 7.7 (4H, m), 7.5 (2H, d), 7.3 (1H, bs), 7.0 (1H, bs).

f) 2-[(Aminocarbonyl)amino]-5-(4-cyanophenyl)-3-thiophenecarboxamide

Prepared by the method of Example 26(b).

MS (ES) 285 (M−H)−. $^1$H NMR(DMSO-D6) 11.0 (1H, bs), 8.0 (1H, s), 7.8 (2H, d), 7.7 (3H, m), 7.4 (1H, bs), 7.0 (2H, bs).

EXAMPLE 57

2-[(Aminocarbonyl)amino]-5-(4-trifluoromethylphenyl)-3-thiophenecarboxamide

Prepared by the methods of Example 56(d-f) but using 4-trifluoromethylphenylboronic acid.

MS (ES) 328 (M–H)$^-$. $^1$H NMR (DMSO-D6) 11.0 (1H, bs), 7.9 (1H, s), 7.7 (5H, m), 7.3 (1H, bs), 7.0 (2H, bs).

EXAMPLE 58

2-[(Aminocarbonyl)amino]-5-(2,4-difluorophenyl)-3-thiophenecarboxamide

Prepared by the method of Example 56(d-f) but using 2,4-difluorophenylboronic acid.

MS (ES) 296 (M–H)$^-$. $^1$H NMR (DMSO-D6) 11.0 (1H, bs), 7.7 (2H, m), 7.6 (1H, m), 7.3 (2H, m), 7.2 (1H, m), 7.0 (2H, bs).

EXAMPLE 59

2-[(Aminocarbonyl)amino]-5-(2-pyridyl)-3-thiophenecarboxamide

Prepared by the method of Example 26(b) from 2-amino-5-(2-pyridyl)-3-thiophenecarboxamide.

MS (ES) 263 (M+H)$^+$. $^1$H NMR (DMSO-D6) 11.04 (1H, s), 8.46-8.41 (1H, m), 7.99 (1H, s), 7.81-7.73 (1H, m), 7.65 (1H, bs), 7.61 (1H, d), 7.27 (1H, bs), 7.19-7.12 (1H, m), 6.95 (2H, bs).

The starting material was prepared as follows:

a) 2-(2-Methoxyyinyl)pyridine

A stirred suspension of methoxymethyltriphenyl phosphonium chloride (12.48 g) in tetrahydrofuran (60 ml) under argon was cooled in an ice-bath. Potassium tert-butoxide (36.41 ml, 1M solution in tetrahydrofuran) was then added dropwise over 30 minutes to give a deep orange-red colour. Stirring was continued at 0-5° C. for 50 minutes then the mixture was cooled to –78° C. 2-Pyridinecarboxaldehyde was added dropwise and stirring continued at –78° C. for a further 2 h then allowed to warm to room temperature and stirred for 2 h. Hexane (100 ml) was added, the mixture filtered and the filtrate evaporated in vacuo. The residue was purified by column chromatography on silica gel eluting, with 10% ethyl acetate in hexane to give the pure cis-2-(2-methoxyvinyl)pyridine (0.91 g, 24%):

$^1$H NMR (CDCl$_3$) 8.51 (1H, d), 7.88 (1H, d), 7.63-7.55 (1H, m), 7.02 (1H, dd), 6.35 (1H, d, J=7 Hz), 5.50 (1H, d, J=7 Hz), 3.84 (3H, s);

and a mixture of cis:trans products (1:1, 2.54 g, 67%):

$^1$H NMR (CDCl$_3$) 8.52-8.49 (0.5H, m), 8.46-8.41 (0.5H, m), 7.86 (0.5H, d), 7.63-7.48 (1.5H, m), 7.07-6.95 (1.5H, m), 6.35 (0.5H, d, J=7 Hz), 5.87 (0.5H, d, J=13 Hz), 5.50 (0.5H, d, J=7 Hz), 3.84 (1.5H, s), 3.73 (1.5H, s).

b) 2-Amino-5-(2-pyridyl)-3-thiophenecarboxamide 2-(2-Methoxyvinyl)pyridine (1.28 g) was dissolved in ethanol (13 ml) and to the solution was added 6M sulphuric acid (3.6 ml). The solution was heated to 80° C. for 20 minutes then allowed to cool to 55° C. Morpholine (8 ml) was added followed by cyanoacetamide (0.796 g) and sulfur (0.334 g). The mixture was heated at 55° C. for 4 h. After cooling to room temperature the solution was poured into water (100 ml) and extracted with ethyl acetate. The extracts were dried (MgSO$_4$), filtered and evaporated. The residue was adsorbed onto silica gel and eluted with 2-5% methanol in dichloromethane to give an orange solid (345 mg, 17%).

MS (ES) 220 (M+H)$^+$. $^1$H NMR (DMSO-D6) 8.36 (1H, dd), 7.83 (1H, s), 7.76-7.67 (1H, m), 7.62 (2H, s), 7.54 (1H, d), 7.25 (1H, bs), 7.12-7.05 (1H, m), 6.83 (1H, bs).

EXAMPLE 60

2-[(Aminocarbonyl)amino]-5-(3-pyridyl)-3-thiophenecarboxamide

Prepared by the method of Example 59 from 3-(2-methoxyvinyl)pyridine.

MS (ES) 263 (M+H)$^+$. $^1$H NMR (DMSO-D6) 11.02 (1H, s), 8.74 (1H, d), 8.41 (1H, dd), 7.84 (1H, dd), 7.82 (1H, s), 7.66 (1H, bs), 7.38 (1H, dd), 7.33 (1H, bs), 6.98 (2H, bs).

3-(2-Methoxyvinyl)pyridine

Prepared by the method of Example 59(a) from 3-pyridinecarboxaldehyde.

1:2.1 cis: trans products.

$^1$H NMR (CDCl$_3$) 8.66 (0.32H, d), 8.47 (0.68H, d), 8.39-8.32 (1H, m), 7.99-7.92 (0.32H, m), 7.55-7.49 (0.68H, m), 7.21-7.12 (1H, m), 7.06 (0.68H, d, J=13 Hz), 6.25 (0.32H, d, J=7 Hz), 5.75 (0.68H, d, J=13 Hz), 5.20 (0.32H, d, J=7 Hz), 3.80 (0.96H, s), 3.70 (2.04H, s).

EXAMPLE 61

2-[(Aminocarbonyl)amino]-5-(4-pyridyl)-3-thiophenecarboxamide

Prepared by the method of Example 59 from 4-(2-methoxyvinyl)pyridine.

MS (ES) 263 (M+H)$^+$. $^1$H NMR (DMSO-D6) 11.09 (1H, s), 8.50 (2H, d), 8.03 (1H, s), 7.72 (1H, bs), 7.44 (2H, d), 7.35 (1H, bs), 7.04 (2H, bs).

4-(2-Methoxyvinyl)pyridine

Prepared by the method of Example 59(a) from 4-pyridinecarboxaldehyde.

1:1.13 cis: trans products.

MS (EI) 135 (M$^+$). $^1$H NMR (CDCl$_3$) 8.48 (0.94H, d), 8.43 (1.06H, d), 7.41 (0.94H, d), 7.25 (0.53H, d, J=14 Hz), 7.08 (1.06H, d), 6.32 (0.47H, d, J=8 Hz), 5.70 (0.53H, d, J=14 Hz), 5.17 (0.47H, d, J=8 Hz), 3.85 (1.41H, s), 3.73 (1.59H, s).

EXAMPLE 62

2-[(Aminocarbonyl)amino]-5-[5-(2-methoxypyridyl]-3-thiophenecarboxamide

Prepared by the method of Example 59 from 2-methoxy-5-(2-methoxyvinyl)pyridine.

MS (ES) 293 (M+H)$^+$. $^1$H NMR (DMSO-D6) 10.96 (1H, bs), 8.27 (1H, d), 7.80 (1H, dd), 7.61 (1H, s), 7.61 (1H, bs), 7.28 (1H, bs), 6.95 (2H, bs), 6.85 (1H, d), 3.84 (3H, s).

2-Methoxy-5-(2-methoxyvinyl)pyridine

Prepared by the method of Example 59(a) from 5-(2-methoxypyridine)carboxaldehyde.

1:1.44 cis:trans products.

MS (EI) 165 (M$^+$). $^1$H NMR (CDCl$_3$) 8.24 (0.41H, d), 7.98 (0.59H, d), 7.91 (0.41H, dd), 7.47 (0.59H, dd), 6.92 (0.59H, d, J=13 Hz), 6.70-6.63 (1H, m), 6.11 (0.41H, d, J=7 Hz), 5.72 (0.59H, d, J=13 Hz), 5.14 (0.41H, d, J=7 Hz), 3.92 and 3.90 (3H, s), 3.76 (1.23H, s), 3.68 (1.77H, s).

The 5-(2-methoxypyridine)carboxaldehyde was prepared as follows:

a) Bromine (0.99 ml) was added dropwise to a stirred suspension of sodium acetate (1.59 g) and 2-methoxypyridine (1.93 ml) in acetic acid (10 ml). The reaction mixture was stirred at room temperature for 25 minutes, then at 80° C. for 2.5 h. The mixture was then allowed to cool and poured into ice-water, neutralised with 2M sodium hydroxide and extracted with ether. The combined extracts were dried (MgSO$_4$), filtered and evaporated. The crude product was purified by column chromatography on silica gel eluting with 5% ethyl acetate in hexane to give 5-bromo-2-methoxypyridine as a colourless oil (1.75 g, 51%).

MS (ES) 190, 188 (M+H)$^+$. $^1$H NMR (CDCl$_3$) 8.20 (1H, d), 7.63 (1H, dd), 6.65 (1H, d), 3.90 (3H, s).

b) 5-Bromo-2-methoxypyridine (1.53 g) was stirred in dry tetrahydrofuran (35 ml) under argon at −78° C. Butyl lithium (6.6 ml, 1.6M solution) was added dropwise to the solution and stirring continued at −78° C. for 1.5 h. Dimethylformamide (1.3 ml) was then added dropwise and stirring continued at −78° C. for a further 30 minutes before allowing to warm to room temperature. The reaction mixture was poured into saturated aqueous sodium hydrogen carbonate and the aqueous phase was extracted with ether. The combined extracts were dried (MgSO$_4$), filtered and evaporated. The residue was purified by column chromatography on silica gel to give 5-(2-methoxypyridine)carboxaldehyde as a white solid (0.91 g, 81%). $^1$H NMR (CDCl$_3$) 9.95 (1H, s), 8.63 (1H, d), 8.06 (1H, dd), 6.85 (1H, d), 4.04 (3H, s).

EXAMPLE 63

2-[(Aminocarbonyl)amino]-5-[5-(2,4-dimethoxypyrimidyl)]-3-thiophenecarboxamide

Prepared by the method of Example 59 from 2,4-dimethoxy-5-(2-methoxyvinyl)-pyrimidine.

MS (ES) 324 (M+H)$^+$. $^1$H NMR(DMSO-D6) 11.01 (1H, s), 8.50 (1H, s), 7.70 (1H, s), 7.69 (1H, bs), 7.31 (1H, bs), 6.95 (2H, bs), 4.05 (3H, s), 3.94 (3H, s).

5-(2,4-Dimethoxypyrimidine)carboxaldehyde

Prepared by the method of Example 62(b) from 5-bromo-2,4-dimethoxypyrimidine.

MS (EI) 168 (M$^+$). $^1$H NMR (CDCl$_3$) 10.17 (1H, s), 8.78 (1H, s), 4.11 (3H, s), 4.09 (3H, s).

2,4-Dimethoxy-5-(2-methoxyvinyl)-pyrimidine

Prepared by the method of Example 59(a) from 5-(2,4-dimethoxypyrimidine)-carboxaldehyde.

29% trans product isolated:

MS (EI) 196 (M$^+$). $^1$H NMR (CDCl$_3$) 8.06 (1H, s), 7.10 (1H, d, J=13 Hz), 5.64 (1H, d, J=13 Hz), 4.02 (3H, s), 3.97 (3H, s), 3.67 (3H, s).

49% cis product isolated:

$^1$H NMR (CDCl$_3$) 8.95 (1H, s), 6.19 (1H, d, J=7 Hz), 5.30 (1H, d, J=7 Hz), 3.97 (6H, s), 3.75 (3H, s).

EXAMPLE 64

2-[(Aminocarbonyl)amino]-5-(4-hydroxyphenyl)-3-thiophenecarboxamide a) 2-Amino-3-thiophenecarboxamide A suspension of 2,5-dihydroxy-1,4-dithiane (25 g) and cyanoacetamide (19.3 g) in ethanol (120 mL) was stirred and heated to 50° C. Triethylamine (9.2 ml) was added over 15 minutes and the mixture was stirred at 50° C. for a further 2 h. After ice cooling the solid was filtered off and dried (21.4 g).

MS (ES) 143 (M+H)$^-$.

b) 2-[(Aminocarbonyl)amino]-3-thiophenecarboxamide

Prepared by the method of Example 26(b) from 2-amino-3-thiophenecarboxamide.

MS (ES) 186 (M+H)$^-$.

c) 2-[(Aminocarbonyl)amino]-5-bromo-3-thiophenecarboxamide

2-[(Aminocarbonyl)amino]-3-thiophenecarboxamide (1.0 g) was dissolved in acetic acid (20 ml) and a solution of bromine (0.35 ml) in acetic acid (5 ml) was added over 5 minutes with rapid stirring. The mixture was stirred for 90 minutes and then added to water (50 ml). The product was filtered off and washed with water and dried under vacuum (0.55 g).

MS (ES) 262/264 (M−H)$^-$. $^1$H NMR (DMSO-D6) 10.63 (1H, s), 7.9 (1H, m), 7.8 (1H, s), 7.35 (1H, m), 7.15 (1H, m).

d) 2-[(Aminocarbonyl)amino]-5-(4-methoxyphenyl)-3-thiophenecarboxamide

A solution of 2-[(aminocarbonyl)amino]-5-bromo-3-thiophenecarboxamide (0.55 g), sodium carbonate (0.44 g) and 4-methoxyphenylboronic acid (0.51 g) in dimethoxyethane (60 ml) and water (2 ml) was purged with argon for 10 minutes. Tetrakis(triphenylphosphine)palladium (0.243 g) was then added and the mixture refluxed with stirring for 18 h. After cooling, the mixture was screened and evaporated. The residue was partitioned between ethyl acetate and 2N sodium hydroxide and the solid interface layer was filtered off (0.2 g).

MS (ES) 290 (M−H)$^+$. $^1$H NMR (DMSO-D6) 10.54 (1H, s), 8.0 (1H, m), 7.9 (1H, s), 7.45 (2H, d), 7.35 (1H, m), 6.95 (2H, d), 3.8 (3H, s).

e) 2-[(Aminocarbonyl)amino]-5-(4-hydroxyphenyl)-3-thiophenecarboxamide

Prepared by the method of Example 9(a).

MS (ES) 276 (M−H)$^-$. $^1$H NMR (DMSO-D6) 10.12 (1H, s), 8.0 (1H, m), 7.85 (1H, s), 7.4 (2H, d), 7.35 (1H, m), 6.9 (2H, d).

EXAMPLE 65

2-[(Aminocarbonyl)amino]-5-(4-chlorophenyl)3-thiophenecarboxamide

Prepared by the method of Example 64(d) using 4-chlorophenylboronic acid.

MS (ES) 294 (M−H)$^-$. $^1$H NMR (DMSO-D6) 10.6(1H, s),8.1(1H, s),7.85(1H, s),7.5(2H, d),7.4(3H, m),7.0(2H, m).

EXAMPLE 66

2-[(Aminocarbonyl)amino]-5-(4-methanesulphonylphenyl)-3-thiophenecarboxamide

Prepared by the method of Example 64(d) using 4-methanesulphonylphenylboronic acid.

MS (ES) 338.28 (M+H)⁻. $^1$H NMR (DMSO-D6) 11.06 (1H, s), 7.95 (1H, s), 7.90 (2H, d), 7.70 (3H, m), 7.35 (1H, s), 7.00 (2H, s), 3.20 (3H, s).

EXAMPLE 67

2-[(Aminocarbonyl)amino]-5-(2-(N-t-butoxycarbonyl)pyrrolyl)-3-thiophenecarboxamide Prepared by the method of Example 64(d) from 1-(t-butoxycarbonyl)pyrrolyl-2-boronic acid.

MS (ES) 351 (M+H)⁺. $^1$H NMR (DMSO-D6) 10.97 (1H, s), 7.55 (1H, s), 7.30 (1H, s), 7.2 (1H, s), 7.18 (1H, s), 6.85 (2H, m), 6.25 (2H, m), 1.40 (9H, s).

EXAMPLE 68

2-[(Aminocarbonyl)amino]-5-(2-(5-cyanothienyl))-3-thiophenecarboxamide

Prepared by the method of Example 64(d) from 5-cyanothiophenyl-2-boronic acid

MS (ES) 291 (M–H)⁻. $^1$H NMR (DMSO-D6) 11.1 (1H, s), 7.89 (1H, s), 7.85 (1H, d), 7.75 (1H, s), 7.4 (1H, s), 7.2 (1H, d), 7.1 (2H, s).

EXAMPLE 69

2-[(Aminocarbonyl)amino]-5-(3,5-dimethyl-isoxazol-4-yl)-3-thiophenecarboxamide

Prepared by the method of Example 64(d) from 3,5 dimethylisoxazolyl-4-boronic acid MS (ES) 279 (M–H)⁻. $^1$H NMR (DMSO-D6) 11.0 (1H, s), 7.8 (1H, s), 7.4 (1H, s), 7.3 (1H, s), 6.9 (2H, s), 2.53 (3H, s), 2.3 (3H, s).

EXAMPLE 70

2-[(Aminocarbonyl)amino]-5-(3-furyl)-3-thiophenecarboxamide

Prepared by the method of Example 64(d) from 3-furylboronic acid.

MS (ES) 250 (M–H)⁻. $^1$H NMR (DMSO-D6) 10.9 (1H, s), 7.9 (1H, s), 7.7 (1H, m), 7.6 (1H, s), 7.4 (1H, s), 7.2 (1H, s), 6.9 (2H, s), 6.5 (1H, m).

EXAMPLE 71

2-[(Aminocarbonyl)amino]-5-(2-pyrrolyl)-3-thiophenecarboxamide

2-[(Aminocarbonyl)amino]-5-(2-(N-t-butoxycarbonyl)pyrrolyl)-3-thiophenecarboxamide (0.1 g), water (0.1 ml) and trifluoroacetic acid (2 ml) were stirred at room temperature for 8 minutes before dropwise addition to saturated aqueous sodium bicarbonate solution (15 ml). The product was extracted into ethyl acetate and the organic layer separated. The crude product was chromatographed on silica gel eluting with methanol/dichloromethane mixtures. The solvent was removed and the product collected (0.04 g).

MS (ES) 249 (M–H)⁻. $^1$H NMR (DMSO-D6) 11.04 (1H, s), 10.86 (1H, s), 7.5(1H, s), 7.2-7.15 (2H, m), 6.85 (2H, s), 6.7(1H, m), 6.15 (1H, m), 6.05 (1H, m).

EXAMPLE 72

2-[(Aminocarbonyl)amino]-5-(5-pyrimidinyl)-3-thiophenecarboxamide

Triisopropyl borate (1.48 ml) was added to a stirred solution of 5-bromopyrimidine (200 mg) in tetrahydrofuran (10 ml) under argon. The solution was then cooled to –78° C. and n-butyl lithium (3.30 ml, 1.6M solution in hexanes) was added dropwise. Stirring was continued at –78° C. for 5 minutes before allowing the reaction mixture to warm to room temperature. The solvent was removed in vacuo, dimethoxyethane (12 ml) was added, followed by 2-[(aminocarbonyl)amino]-5-bromo-3-thiophenecarboxamide (200 mg) and saturated aqueous sodium hydrogen carbonate (3.5 ml). The flask was purged with argon and tetrakis(triphenylphosphine) palladium (0) (90 mg) added. The mixture was heated at 90° C. for 4 h, then allowed to cool. The solvent was removed in vacuo and the residue taken up in 2M sodium hydroxide and 10% methanol in dichloromethane. The layers were separated and the aqueous phase was filtered to remove a small amount of insoluble material. The filtrate was then neutralised with 6M hydrochloric acid and the precipitate formed collected by filtration, washed with water and dried. The product was then triturated with methanol, collected by filtration and dried under high vacuum (47 mg, 24%).

MS (ES) 264 (M+H)⁺. $^1$H NMR (DMSO-D6) 11.02 (1H, bs), 9.01 (1H, s), 8.91 (2H, s), 7.93 (1H, s), 7.66 (1H, bs), 7.39 (1H, bs), 7.04 (2H, bs).

EXAMPLE 73

2-[(Aminocarbonyl)amino]-5-(2-(5-chlorothienyl))-3-thiophenecarboxamide

Prepared by the method of Example 72 using 5-chloro-2-bromothiophene.

MS(ES) 300.18 (M–H)⁻.

1H NMR (DMSO-D6) 11.0(1H, s), 7.75(1H, s), 7.50(1H, s), 7.25(1H, s), 7.0(1H, d), 6.95 (3H, d+bs).

EXAMPLE 74

2-[(Aminocarbonyl)amino]-5-[2-(5-trifluoromethylpyridyl)]-3-thiophenecarboxamide Prepared in a similar manner to Example 72 from 2-bromo-5-trifluoromethylpyridine.

MS (ES) 331 (M+H)⁺. $^1$H NMR (DMSO-D6, 400 MHz) 11.17 (1H, s), 8.85 (1H, s), 8.26 (1H, s), 8.21 (1H, d), 7.83 (1H, d), 7.76 (1H, bs), 7.39 (1H, bs), 7.07 (2H, bs).

EXAMPLE 75

2-[(Aminocarbonyl)amino]-5-[2-(5-bromopyridyl)]-3-thiophenecarboxamide

Prepared in a similar manner to Example 72 from 2,5-dibromopyridine.

MS (ES) 343, 341 (M+H)$^+$. $^1$H NMR (DMSO-D6, 500 MHz) 11.07 (1H, s), 8.55 (1H, d), 8.03 (1H, s), 8.02 (1H, dd), 7.63 (1H, bs), 7.58 (1H, d), 7.26 (1H, bs), 6.95 (2H, bs).

EXAMPLE 76

2-[(Aminocarbonyl)amino]-5-(2-(5-cyanofuryl))-3-thiophenecarboxamide

Prepared by the method of Example 72 using 5-cyano-2-bromofuran.

MS(ES) 275 (M−H)$^−$. 1H NMR (DMSO-D6) 11.1 (1H, bs), 7.85 (1H, s), 7.8 (1H, bs), 7.6 (1H, d), 7.35 (1H, bs), 7.1 (2H, bs), 6.75 (1H, d).

EXAMPLE 77

2-[(Aminocarbonyl)amino]-5-(4-[2-(1-piperidinyl)ethoxy]phenyl)-3-thiophenecarboxamide Prepared as in Example 72 using 4-[2-(1-piperidinyl)ethoxy]bromobenzene.

MS(ES) 389(M+H)$^+$. $^1$H NMR (DMSO-D6) 10.98 (1H, s), 7.62 (1H, s), 7.6 (1H, s), 7.42 (2H, d), 7.25 (1H, d), 6.98 (2H, d), 6.9 (2H, s), 4.15 (2H, m), 1.6 (4H, M), 1.42 (2H, m).

4-[2-(1-Piperidinyl)ethoxy]bromobenzene was prepared as follows:— a) 4-Bromophenol (1 g), N-(2-chloroethyl)piperidine hydrochloride (0.94 g) and potassium carbonate (1.76 g) in dimethylformamide (15 ml) were stirred and heated at 60° C. for 15 h. The reaction mixture was cooled and partitioned between ethyl acetate and water. The separated solvent phase was washed twice with 2N sodium hydroxide, once with saturated brine and then dried (MgSO$_4$). The resulting oil was used without further purification.

MS (ES) 284 (M+H)$^+$. $^1$H NMR (DMSO-D6) 7.2 (2H, d), 6.9 (2H, d), 4.05 (2H, m), 2.62 (2H, t), 2.38 (4H, m), 1.48(4H, m), 1.36 (2H, m).

EXAMPLE 78

2-[(Aminocarbonyl)amino]-5-(4-[2-(1-(2,2,6,6-tetramethyl)piperidinyl)ethoxy]phenyl)-3-thiophenecarboxamide Prepared as in Example 72 using 4-[2-(2,2,6,6-tetramethyl-1-piperidinyl)ethoxy]bromobenzene which was prepared in a similar manner to Example 77(a).

MS(ES) 445(M+H)$^+$. $^1$H NMR (DMSO-D6) 7.48 (2H, d), 6.96 (2h, d), 4.22 (2H, m), 3.62 (2H, m), 1.8 (4H, m), 1.56 (2H, m), 1.42 (6H, s), 1.36 (6H, s).

EXAMPLE 79

2-[(Aminocarbonyl)amino]-5-(4-(thiazol-4-yl-methoxy)phenyl)-3-thiophenecarboxamide Prepared as in Example 72 using 4-[thiazol-4-yl-methoxy]bromobenzene which was prepared in a similar manner to Example 77(a).

MS(ES) 375(M+H)$^+$. $^1$H NMR (DMSO-D6) 10.91 (1 h, s), 9.1 (1H, s), 7.88 (1H, s), 7.82 (1H, bs), 7.75 (1H, s), 7.42 (2H, d), 7.24 (1H, bs), 7.08 (2H, d), 6.9 (1H, bs), 5.11 (2H, s).

EXAMPLE 80

2-[(Aminocarbonyl)amino]-5-(4-[2-(dimethylamino)ethoxy]phenyl)-3-thiophenecarboxamide Prepared as in Example 72 using 4-[2-(dimethylamino)ethoxy]bromobenzene which was prepared in a similar manner to Example 77(a).

MS(ES) 349(M+H)$^+$. $^1$H NMR (DMSO-D6) 11 (1H, s), 7.65 (1H, bs), 7.6 (1H, s), 7.5 (2H, d), 7.28(1H, bs), 7.05 (2H, d), 6.9(2H, bs), 4.45 (2H, t), 3.5 (2H, t), 2.85 (6H, s).

EXAMPLE 81

2-[(Aminocarbonyl)amino]-5-(4-[2-(diethylamino)ethoxy]phenyl)-3-thiophenecarboxamide Prepared as in Example 72 using 4-[2-(dimethylamino)ethoxy]bromobenzene which was prepared in a similar manner to Example 77(a).

MS(ES) 377(M+H)$^+$. $^1$H NMR (DMSO-D6) 11 (1H, s), 7.65 (1H, bs), 7.6 (1H, s), 7.5 (2H, d), 7.28 (1H, bs), 7.05 (2H, d), 6.9 (2H, bs), 4.35 (2H, t), 3.5 (2H, t), 3.25 (4H, m), 1.2 (6H, t).

EXAMPLE 82

2-[(Aminocarbonyl)amino]-5-(4-[2-(1-morpholinyl)ethoxy]phenyl)-3-thiophenecarboxamide Prepared as in Example 72 using 4-[2-(1-morpholinyl)ethoxy]bromobenzene which was prepared in a similar manner to Example 77(a).

MS(ES) 391 (M+H)$^+$. $^1$H NMR (DMSO-D6)10.9 (1H, s), 7.55 (1H, s), 7.5 (2H, d), 7.15 (1H, bs), 7.05 (2H, d), 6.55 (2H, bs), 4.4 (2H, s), 3.8 (4H, s), 3.4-2.8 (6H, bm).

EXAMPLE 83

2-[(Aminocarbonyl)amino]-5-(2-furyl)-3-thiophenecarboxamide

To a solution of furan (598 mg) in dry tetrahydrofuran (15 ml) cooled to −75° C. under argon was added dropwise n-butyl lithium (7.16 ml, 1.6M solution in hexanes). The mixture was allowed to warm to −10° C. and stirred at this temperature for 1 h. The mixture was cooled to −60° C. and triisopropyl borate (3.04 ml) was added and after the addition the mixture was allowed to warm to room temperature and stirred for a further 0.5 h. The mixture was concentrated and dimethoxyethane (12 ml), 2-[(aminocarbonyl)amino]-5-bromo-3-thiocarboxamide and saturated sodium bicarbonate (5.5 ml) were added. The mixture was purged with argon and tetrakis(triphenylphosphine) palladium (0) (150 mg)

was added and then refluxed under argon atmosphere for 4 h. The mixture was concentrated and then partitioned between ethyl acetate and 2N sodium hydroxide. The organic layer was dried (MgSO$_4$) and evaporated. The residue was purified by column chromatography on silica gel eluting with methanol/methylene chloride mixture to give the title compound as a solid (152 mg).

MS (ES) 235 (M–NH$_2$)$^+$. $^1$H NMR (DMSO-D6) 7.7 (1H, bs), 7.65 (1H, s), 7.5 (1H, s), 7.3 (1H, bs), 7.25 (1H, bs), 7.0 (2H, bs), 6.5 (2H, dd).

EXAMPLE 84

2-[(Aminocarbonyl)amino]-5-(2-(5-methylfuryl))-3-thiophenecarboxamide

Prepared in a similar manner to Example 83 from 2-methylfuran.

MS (ES) 266 (M+H)$^+$. $^1$H NMR (DMSO-D6) 11.0 (1H, bs), 7.7 (1H, bs), 7.4 (1H, s), 7.2 (1H, bs), 6.95 (2H, bs), 6.35 (1H, d), 6.1 (1H, d), 2.3 (3H, s).

EXAMPLE 85

5-[(Aminocarbonyl)amino]-2-(3,5-dichlorophenyl)-1,3-oxazole-4-carboxamide

Prepared as in Example 26(b) from 5-amino-2-(3,5-dichlorophenyl)-1,3-oxazole-4-carboxamide.

NMR (DMSO-D6) 7.8 (2H, s), 7.75 (1H, s), 7.54 (1H, bs), 7.43 (1H, bs), 6.81 (2H, bs) MS (M+H)+315.2/317.9.

The starting material was prepared as follows:

Concentrated sulphuric acid (5 ml) was added to 5-amino-2-(3,5-dichlorophenyl)-1,3-oxazole-4-carbonitrile (490 mg) at 0° C. After stirring at ambient temperature for 90 minutes the mixture was poured onto ice and neutralised by addition of potassium carbonate. The mixture was extracted with ethyl acetate which was then dried (MgSO$_4$) and evaporated under reduced pressure to yield a pale yellow solid (420 mg, 80%).

NMR (DMSO-D6) 7.67.(2H, s), 7.63 (1H, s), 7.15 (2H, bs), 6.99 (2H, bs). MS (M+Na)+294.23/296.22.

EXAMPLE 86

5-[(Aminocarbonyl)amino]-2-(4-trifluoromethylphenyl)-1,3-oxazole-4-carboxamide Prepared as Example 26(b) from 5-amino-2-(4-(trifluoromethyl)phenyl)-1,3-oxazole-4-carboxamide to yield a cream solid (54%).

NMR (DMSO-D6) 9.26 (1H, bs), 8.08 (2H, d) 7.91 (2H, d), 7.52 (1H, bs), 7.43 (1H, bs), 6.79 (2H, bs).

MS(ES) (M+H)+315.28.

The starting material was made as in Example 85 but starting from 5-amino-2-(4-(trifluoromethyl)phenyl)-1,3-oxazole-4-carbonitrile to yield a cream solid (61%).

NMR (DMSO-D6) 7.93 (2H, d), 7.82 (2H, d), 7.16 (2H, bs) 6.99 (1H, bs). MS (M–H)$^-$270.3.

EXAMPLE 87

2-[(Aminothiocarbonyl)amino-5-phenyl-3-thiophenecarboxamide

A solution of 2-amino-5-phenyl-3-thiophenecarboxamide (1.09 g, 5 mmol) and trimethylsilyl isothiocyanate (0.85 ml, 6 mmol) in N,N-dimethylacetamide was stirred at 75° C. for 7 days. N,N-Dimethylformamide was added until solution. The solvent was removed and the resulting slurry was chromatographed on silica gel eluting with isohexane followed by methylene chloride and diethyl ether to give the product as a yellow solid (0.49 g, 35%).

$^1$H NMR (DMSO-D6, 300MHz) δ 12.59 (1H, s), 8.40 (2H, s), 7.85 (1H, s), 7.77 (1H, s), 7.53 (3H, d+s), 7.39 (2H, t), 7.25 (1H, t). MS (ES) 278 (M+H)$^+$.

PHARMACOLOGICAL EVALUATION OF COMPOUNDS

IKK2 Filter Kinase Assay

Compounds were tested for inhibition of IKK2 using a filter kinase assay. The test compounds were dissolved to 10 mM in dimethylsulphoxide (DMSO). The compounds were then diluted 1 in 40 in kinase buffer (50 mM Tris, pH 7.4 containing 0.1 mM EGTA, 0.1 mM sodium orthovanadate and 0.1% β-mercaptoethanol). 1 in 3 serial dilutions were made from this solution with 2.5% DMSO in kinase buffer. 20 µl of compound dilution was added to wells of a 96 well plate in duplicate. 20 µl 2.5% DMSO in kinase buffer instead of compound was added to control wells (0% inhibition). 20 µl 0.5 M EDTA was added instead of compound to background wells (100% inhibition).

10 µl of a mixture of magnesium acetate, unlabelled ATP, and $^{33}$P-labelled ATP was added to each well made such that the final concentration was 10 mM magnesium acetate, 1 µM ATP and 0.1 µCi $^{33}$P ATP. 20 µl of a mixture of IKK2 (0.15 µg/well), 1-53 GST-IκB (0.5 µg/well) and bovine serum albumin (BSA) (8.5 µg/well) was added to each well to start the reaction. The final reaction volume was 50 µl.

The kinase reactions were incubated at 21° C. for 80 minutes and the reaction stopped by precipitating the protein by the addition of an equal volume (50 µl) of 20% trichloroacetic acid (TCA). The precipitate was allowed to form for 10 minutes and then filtered onto a GF/C unifilter 96 well plate. Each filter was washed twice with approximately 1 ml 2% TCA. The filter plate was dried at 30-40° C. for 60 minutes, 20 µl scintillant was added to each well and the plate sealed and radioactivity counted on a Packard Topcount microplate scintillation counter.

IKK1 Filter Kinase Assay

The selectivity of compounds was assessed by testing them for inhibition of IKK1 using a filter kinase assay. The assay conditions were identical to the IKK2 filter kinase assay except that a mixture of IKK1 (0.25 µg/well) and 1-53 GST IκB (9 µg/well) was added to each well to start the reaction.

Inhibition of LPS-induced TNFα Production by PBMCs

The effect of test compounds on nuclear factor kappa B (NFκB) activation in cells was assessed by measuring inhibition of tumour necrosis factor alpha (TNFα) production by human peripheral blood mononuclear cells (PBMCs) stimulated by bacterial lipopolysaccharide (LPS).

Human blood (250 ml), anticoagulated with heparin, was collected from healthy volunteers. Aliquots of blood (25 ml) were layered on 20 ml Lymphoprep (Nycomed) in 50 ml polypropylene centrifuge tubes. The tubes were centrifuged (Sorval RT600B) at 2,500 rpm for 30 minutes. The cloudy layer containing PBMCs was collected with a fine tipped Pasteur pipette, transferred into 8 clean polypropylene centrifuge tubes (approximately 10 ml per tube) and diluted to 50 ml with phosphate-buffered saline (PBS). These tubes were centrifuged at 2,000 rpm for 8 minutes. PBS (10 ml) was added to each cell pellet and the cells were gently re-suspended. The cells were pooled in 4 centrifuge tubes, PBS was added to each tube to make the volume up to 50 ml and the tubes were centrifuged at 1,400 rpm for 8 minutes. The cell pellets were again re-suspended in 10 ml PBS, pooled in 2 centrifuge tubes, the volume made up to 50 ml with PBS and the tubes centrifuged at 900 rpm for 10 minutes.

The final cell pellets were gently re-suspended in 10 ml tissue culture medium (RPMI containing 1% heat-inactivated human serum, L-glutamine and penicillin and streptomycin), combined into 1 tube and the volume made up to 30 ml with RPMI medium. The cells were counted and the cell suspension was diluted to $2.6 \times 10^6$ cells/ml.

Test compounds were dissolved in DMSO to 10 mM and diluted 1 in 250 (40 µM) with to RPMI medium. The compounds were then serially diluted 1 in 3 with 0.4% DMSO in RPMI medium. Aliquots of test compound dilutions (50 µl) were transferred to the wells of a 96-well plate. Control wells contained 0.4% DMSO in RPMI instead of compound.

Aliquots of the cell suspension (100 µl) were added to each well and the plates incubated at 37° C. for 30 minutes. 50 µl of 40 µg/ml LPS (Sigma, L-4130) was added to wells to stimulate TNFα production by the cells and the plates were incubated overnight at 37° C. RPMI medium (50 µl) was added to negative control wells instead of LPS. The final incubation volume was 200 µl.

Plates were centrifuged for 4 minutes at 1,200 rpm and supernatants were removed for measurement of TNFα concentration. Viability of the remaining cell pellet was measured using WST-1 reagent (Boehringer Mannheim, 1044807). 100 µl RPMI medium containing 10 µl WST-1 reagent was added to each well and the plates were incubated for 0.5 to 3 h. The absorbance at 450 nm was then measured using a 96-well plate spectrophotometer.

TNFα in the supernatants (freshly harvested or stored frozen at −20° C.) were measured using an enzyme-linked immmunosorbant assay (ELISA). The ELISA plate was prepared by coating the wells of a 96 well plate with a sheep anti-human TNFα monoclonal antibody (100 µl of 1 µg/ml antibody diluted in coating buffer; 0.5 M carbonate/bicarbonate buffer, pH 9.6 containing 0.2 g/l sodium azide) and incubating overnight at 4° C. Blank wells were not coated. The wells were washed once with 0.1% BSA in PBS containing 0.05% Tween (PBS/Tween) then incubated for 1 h at room temperature with 1% BSA in coating buffer (200 µl). The wells were then washed 3 times with 0.1% BSA in PBS/Tween.

The samples of supernatant from the PBMC incubation were diluted 1 in 3 with 1% BSA in PBS/Tween. 100 µl aliquots of these dilutions were added to the ELISA plate. Other wells contained 100 µl TNFα standard (10, 3.3, 1.1, 0.37, 0.12, 0.04, 0.014 and 0 ng/ml). The ELISA plate was incubated at room temperature for 2 h before the wells were washed 3 times with 0.1% BSA in PBS/Tween. A rabbit anti-human TNFα antibody (100 µl of a 2.5 µg/ml solution) was added to each well and the plate incubated at room temperature for 1.5 h. The wells were then washed 3 times with 0.1% BSA in PBS/Tween. Goat anti-rabbit IgG-horse radish peroxidase conjugate (ICN, 674371; 100 µl of a 1 in 10,000 dilution) was added to each well and the plate incubated at room temperature for 1.5 h. The wells were washed 3 times with 0.1% BSA in PBS/Tween.

Peroxidase substrate was prepared by dissolving a 1 mg TMB tablet (Sigma, T-5525) in 100 µl DMSO (100 µl) and adding this and 36 µl UHPO (BDH, 30559; 1 g tablet dissolved in 25 ml distilled water) to 10 ml 0.1M citrate/aceate buffer, pH6. 100 µl substrate was added to each well and the plate incubated in the dark at room temperature for approximately 30 minutes. The reaction was stopped by adding 25 µl 2 M sulphuric acid to each well. The absorbance at 450 nm was measured in a 96 well plater spectrophotometer.

The invention claimed is:

1. A compound of formula (I)

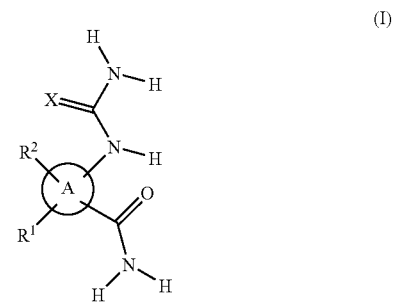

A represents thiophene;

$R^1$ represents a phenyl group; said phenyl being optionally substituted by one or more substituents selected independently from halogen, cyano, nitro, —$NR^3R^4$, —$CONR^5R^6$, —$COOR^7$, —$NR^8COR^9$, —$SR^{10}$, —$S(O)_mR^{10}$, —$S(O)_2NR^5R^6$, —$NR^8SO_2R^{10}$, $C_1$-$C_6$ alkyl, trifluoromethyl, —$(CH_2)_nR^{11}$, —$O(CH_2)_nR^{11}$ or —$OR^{12}$;

$R^2$ represents hydrogen, halogen, cyano, nitro, —$NR^{13}R^{14}$, —$CONR^{15}R^{16}$, —$COOR^{17}$, —$NR^{18}COR^{19}$, —$S(O)_mR^{20}$, —$S(O)_2NR^{15}R^{16}$, —$NR^{18}SO_2R^{20}$, $C_1$-$C_2$ alkyl, trifluoromethyl, $C_2$-$C_3$ alkenyl, $C_2$-$C_3$ alkynyl, trifluoromethoxy, $C_1$-$C_2$ alkoxy or $C_1$-$C_2$ alkanoyl;

X represents oxygen or sulphur;

each of $R^3$, $R^4$, $R^5$, $R^6$, $R^7$, $R^8$, $R^9$, $R^{10}$ and $R^{12}$ independently represent a hydrogen atom or $C_1$-$C_6$ alkyl;

$R^{11}$ represents $NR^{21}R^{22}$ where $R^{21}$ and $R^{22}$ are independently hydrogen or $C_1$-$C_6$ alkyl optionally substituted by $C_1$-$C_4$ alkoxy; or $R^{21}$ and $R^{22}$ together with the nitrogen atom to which they are attached form a 5- or 6-membered saturated ring optionally containing a further O, S or $NR^{23}$ group where $R^{23}$ is hydrogen or $C_1$-$C_6$ alkyl; or $R^{11}$ represents $OR^{24}$ where $R^{24}$ represents $C_1$-$C_6$ alkyl;

each of $R^{13}$, $R^{14}$, $R^{15}$, $R^{16}$, $R^{17}$, $R^{18}$, $R^{19}$ and $R^{20}$ independently represent a hydrogen atom or $C_1$-$C_2$ alkyl;

m represents an integer 0, 1 or 2;

n represents an integer 2, 3 or 4;

and optical isomers, racemates, or tautomers thereof or pharmaceutically acceptable salts or solvates thereof.

2. A compound of formula (I), according to claim 1, wherein X represents oxygen.

3. A compound of formula (I), according to claim 1, in which the group A is substituted as shown below in formula (Ia), where B and D are selected from $CR^2$ and S, where $R^2$ is as defined in claim 1 and $R^{25}$ is hydrogen or $C_1$-$C_6$ alkyl:

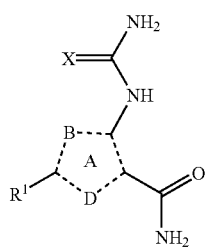

4. A compound according to claim 1 in which $R^2$ represents H or methyl.

5. A compound according to claim 4 in which $R^2$ represents H.

6. A compound of formula (I), according to claim 1, selected from:

- 3-[(aminocarbonyl)amino]-5-phenyl-2-thiophenecarboxamide;
- 3-[(aminocarbonyl)amino]-5-(3-chlorophenyl)-2-thiophenecarboxamide;
- 3-[(aminocarbonyl)amino]-5-(4-fluorophenyl)-2-thiophenecarboxamide;
- 3-[(aminocarbonyl)amino]-5-(4-chlorophenyl)-2-thiophenecarboxamide;
- 3-[(aminocarbonyl)amino]-5-(4-isobutylphenyl)-2-thiophenecarboxamide;
- 3-[(aminocarbonyl)amino]-5-(4-methoxyphenyl)-2-thiophenecarboxamide;
- 3-[(aminocarbonyl)amino]-5-(3-hydroxyphenyl)-2-thiophenecarboxamide;
- 3-[(aminocarbonyl)amino]-5-(2-chlorophenyl)-2-thiophenecarboxamide;
- 3-[(aminocarbonyl)amino]-5-(2-methoxyphenyl)-2-thiophenecarboxamide;
- 3-[(aminocarbonyl)amino]-5-{2-[2-(dimethylamino)ethoxy]phenyl}-2-thiophenecarboxamide;
- 3-[(aminocarbonyl)amino]-5-{4-[2-(dimethylamino)ethoxy]phenyl}-2-thiophenecarboxamide;
- 3-[(aminocarbonyl)amino]-5-(3-methoxyphenyl)-2-thiophenecarboxamide;
- 2-[(aminocarbonyl)amino]-5-phenyl-3-thiophenecarboxamide;
- 3-[(aminocarbonyl)amino]-5-{4-[2-(1-morpholinyl)ethoxy]phenyl}-2-thiophenecarboxamide;
- 3-[(aminocarbonyl)amino]-5-{4-[2-(1-pyrrolidinyl)ethoxy]phenyl}-2-thiophenecarboxamide;
- 3-[(aminocarbonyl)amino]-5-{4-[2-(1-piperidinyl)ethoxy]phenyl}-2-thiophenecarboxamide;
- 3-[(aminocarbonyl)amino]-5-{4-[3-(dimethylamino)propoxy]phenyl}-2-thiophenecarboxamide;
- 3-[(aminocarbonyl)amino]-5-{3-[2-(dimethylamino)ethoxy]phenyl}-2-thiophenecarboxamide;
- 3-[(aminocarbonyl)amino]-5-{3-[2-(1-morpholinyl)ethoxy]phenyl}-2-thiophenecarboxamide;
- 3-[(aminocarbonyl)amino]-5-{3-[2-(1-pyrrolidinyl)ethoxy]phenyl}-2-thiophenecarboxamide;
- 3-[(aminocarbonyl)amino]-5-{3-[2-(1-piperidinyl)ethoxy]phenyl}-2-thiophenecarboxamide;
- 3-[(aminocarbonyl)amino]-5-{3-[3-(dimethylamino)propoxy]phenyl}-2-thiophenecarboxamide;
- 3-[(aminocarbonyl)amino]-5-{2-[2-(1-morpholinyl)ethoxy]phenyl}-2-thiophenecarboxamide;
- 3-[(aminocarbonyl)amino]-5-{2-[2-(1-pyrrolidinyl)ethoxy]phenyl}-2-thiophenecarboxamide;
- 3-[(aminocarbonyl)amino]-5-{2-[2-(1-piperidinyl)ethoxy]phenyl}-2-thiophenecarboxamide;
- 3-[(aminocarbonyl)amino]-5-{2-[3-(dimethylamino)propoxy]phenyl}-2-thiophenecarboxamide;
- 2-[(aminocarbonyl)amino]-4-methyl-5-(4-chlorophenyl)-3-thiophenecarboxamide;
- 2-[(aminocarbonyl)amino]-4-methyl-5-(4-methylphenyl)-3-thiophenecarboxamide;
- 2-[(aminocarbonyl)amino]-4-ethyl-5-phenyl-3-thiophenecarboxamide;
- 2-[(aminocarbonyl)amino]-4-methyl-5-(4-methoxyphenyl)-3-thiophenecarboxamide;
- 2-[(aminocarbonyl)amino]-4-methyl-5-(4-fluorophenyl)-3-thiophenecarboxamide;
- 2-[(aminocarbonyl)amino]-4-methyl-5-(3-fluorophenyl)-3-thiophenecarboxamide;
- 2-[(aminocarbonyl)amino]-4-methyl-5-(3-methoxyphenyl)-3-thiophenecarboxamide;
- 2-[(aminocarbonyl)amino]-4-methyl-5-(3-chloro-4-methoxyphenyl)-3-thiophenecarboxamide;
- 2-[(aminocarbonyl)amino]-4-methyl-5-(2-chlorophenyl)-3-thiophenecarboxamide;
- 2-[(aminocarbonyl)amino]-4-methyl-5-(3-trifluoromethylphenyl)-3-thiophenecarboxamide;
- 2-[(aminocarbonyl)amino]-4-methyl-5-(3-methyl-4-methoxyphenyl)-3-thiophenecarboxamide;
- 2-[(aminocarbonyl)amino]-4-methyl-5-(3,5-dimethoxyphenyl)-3-thiophenecarboxamide;
- 2-[(aminocarbonyl)amino]-4-methyl-5-(2,3-dimethoxyphenyl)-3-thiophenecarboxamide;
- 2-[(aminocarbonyl)amino]-4-methyl-5-(4-isopropylphenyl)-3-thiophenecarboxamide;
- 2-[(aminocarbonyl)amino]-4-methyl-5-(3,4,5-trimethoxyphenyl)-3-thiophenecarboxamide;
- 2-[(aminocarbonyl)amino]-4-methyl-5-(3,4-dichlorophenyl)-3-thiophenecarboxamide;
- 2-[(aminocarbonyl)amino]-4-methyl-5-(4-cyanophenyl)-3-thiophenecarboxamide;
- 2-[(aminocarbonyl)amino]-4-methyl-5-(4-hydroxyphenyl)-3-thiophenecarboxamide;
- 2-[(aminocarbonyl)amino]-4-methyl-5-(4-[2-(1-piperidinyl)ethoxy]phenyl)-3-thiophenecarboxamide;
- 2-[(aminocarbonyl)amino]-4-methyl-5-(4-[2-(diethylamino)ethoxy]phenyl)-3-thiophenecarboxamide;
- 2-[(aminocarbonyl)amino]-4-trifluoromethyl-5-phenyl-3-thiophenecarboxamide;
- 2-[(aminocarbonyl)amino]-4-methyl-5-phenyl-3-thiophenecarboxamide;
- 2-[(aminocarbonyl)amino]-5-(4-cyanophenyl)-3-thiophenecarboxamide;
- 2-[(aminocarbonyl)amino]-5-(4-trifluoromethylphenyl)-3-thiophenecarboxamide;
- 2-[(aminocarbonyl)amino]-5-(2,4-difluorophenyl)-3-thiophenecarboxamide;
- 2-[(aminocarbonyl)amino]-5-(4-hydroxyphenyl)-3-thiophenecarboxamide;
- 2-[(aminocarbonyl)amino]-5-(4-chlorophenyl)-3-thiophenecarboxamide;
- 2-[(aminocarbonyl)amino]-5-(4-methanesulphonylphenyl)-3-thiophenecarboxamide;
- 2-[(aminocarbonyl)amino]-5-(4-[2-(1-piperidinyl)ethoxy]phenyl)-3-thiophenecarboxamide;
- 2-[(aminocarbonyl)amino]-5-(4-[2-(dimethylamino)ethoxy]phenyl)-3-thiophenecarboxamide;

2-[(aminocarbonyl)amino]-5-(4-[2-(diethylamino)ethoxy]phenyl)-3-thiophenecarboxamide;
2-[(aminocarbonyl)amino]-5-(4-[2-(1-morpholinyl)ethoxy]phenyl)-3-thiophenecarboxamide;
2-[(aminothiocarbonyl)amino-5-phenyl-3-thiophenecarboxamide;
and pharmaceutically acceptable salts and solvates thereof.

7. A process for the preparation of a first compound of formula (I), according to claim 1, which comprises:
(a) reaction of a compound of formula (II):

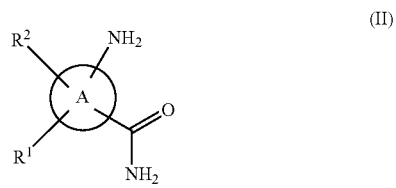

(II)

wherein A, R¹ and R² are as defined in claim 1, with an isocyanate (X═O) or an isothiocyanate (X═S), to produce the first compound of formula (I); or
(b) reaction of compound of formula (III) with a compound of formula (IV)

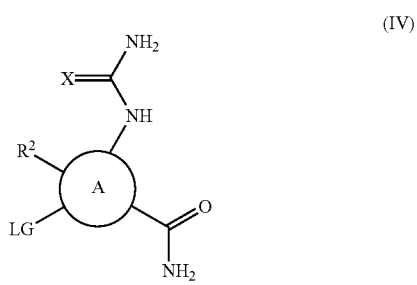

(IV)

wherein A, X, R¹ and R² are as defined in claim 1, and LG represents a leaving group, to produce the first compound of formula (I); or
(c) reaction of compound of formula (V) with a compound of formula (VI)

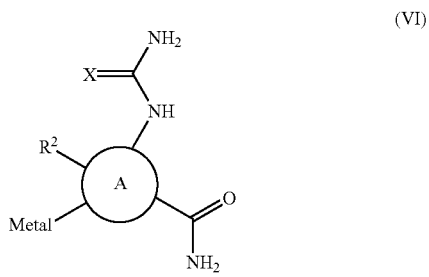

(VI)

wherein A, X, R¹ and R² are as defined in claim 1, and LG represents a leaving group, to produce the first compound of formula (I).

8. A pharmaceutical composition comprising a compound of formula (I), or a pharmaceutically acceptable salt or solvate thereof, as claimed in claim 1, in association with a pharmaceutically acceptable adjuvant, diluent or carrier.

9. A process for the preparation of a pharmaceutical composition which comprises mixing a compound of formula (I), or a pharmaceutically acceptable salt or solvate thereof, as claimed in claim 1 with a pharmaceutically acceptable adjuvant, diluent or carrier.

10. A method of treating an inflammatory disease, selecting from the group consisting of asthma, rheumatoid arthritis, multiple sclerosis, chronic obstructive pulmonary disease, and rhinitis, in a patient suffering from, or at risk of, said disease, which comprises administering to the patient a therapeutically effective amount of a compound of formula (I), or a pharmaceutically acceptable salt or solvate thereof, as claimed in claim 1.

11. A pharmaceutical composition comprising a compound of formula (I), or a pharmaceutically acceptable salt or solvate thereof, as claimed in claim 8, in association with a pharmaceutically acceptable adjuvant, diluent or carrier.

12. A process of claim 7, further comprising converting the first compound of formula (I), or a salt thereof, into a pharmaceutically acceptable salt thereof; or converting the first compound of formula (I) into a second compound of formula (I).

13. A process of claim 7, further comprising converting the first compound of formula (I) into an optical isomer thereof.

14. A compound selected from:
2-[(aminocarbonylamino]-5-(4-[2-(1-(2,2,6,6-tetramethyl)piperidinyl)ethoxy]phenyl)-3-thiophenecarboxamide; and
2-[(aminocarbonylamino]-5-(4-(thiazol-4-yl)methoxy]phenyl)-3-thiophenecarboxamide, or pharmaceutically acceptable salts and solvates thereof.

15. A pharmaceutical composition comprising a compound as defined in claim 14 or a pharmaceutically acceptable salt or solvate thereof, in association with a pharmaceutically acceptable adjuvant, diluent or carrier.

16. A process for the preparation of a pharmaceutical composition which comprises mixing a compound as defined in claim 14 or a pharmaceutically acceptable salt or solvate thereof with a pharmaceutically acceptable adjuvant, diluent or carrier.

17. A method of treating an inflammatory disease selected from asthma, rheumatoid arthritis, multiple sclerosis, chronic obstructive pulmonary disease or rhinitis, in a patient suffering from, or at risk of said disease, which comprises administering to the patient a therapeutically effective amount of a compound as defined in claim 14, or a pharmaceutically acceptable salt or solvate thereof.

* * * * *